(12) United States Patent
Hortobágyi et al.

(10) Patent No.: US 12,195,434 B2
(45) Date of Patent: Jan. 14, 2025

(54) PROCESS FOR THE PREPARATION OF A CHIRAL PROSTAGLANDIN ENOL INTERMEDIATE AND INTERMEDIATE COMPOUNDS USEFUL IN THE PROCESS

(71) Applicant: EUROAPI HUNGARY LIMITED LIABILITY COMPANY, Budapest (HU)

(72) Inventors: Irén Hortobágyi, Budapest (HU); Zsuzsanna Kardos, Budapest (HU); Mariusz Kertész, Budapest (HU); István Lászlófi, Budapest (HU); Ildikó Meleg, Budapest (HU); Judit Póti, Budapest (HU); Andrea Sántáné Csutor, Budapest (HU); László Takács, Budapest (HU)

(73) Assignee: EUROAPI HUNGARY LIMITED LIABILITY COMPANY, Budapest (HU)

( * ) Notice: Subject to any disclaimer, the term of this patent is extended or adjusted under 35 U.S.C. 154(b) by 0 days.

(21) Appl. No.: 17/787,207

(22) PCT Filed: Dec. 16, 2020

(86) PCT No.: PCT/HU2020/050058
§ 371 (c)(1),
(2) Date: Jun. 17, 2022

(87) PCT Pub. No.: WO2021/123848
PCT Pub. Date: Jun. 24, 2021

(65) Prior Publication Data
US 2023/0111101 A1   Apr. 13, 2023

(30) Foreign Application Priority Data
Dec. 18, 2019 (HU) .................................. P1900434

(51) Int. Cl.
*C07D 307/935* (2006.01)
(52) U.S. Cl.
CPC .............................. *C07D 307/935* (2013.01)
(58) Field of Classification Search
CPC .................................................. C07D 307/935
See application file for complete search history.

(56) References Cited

U.S. PATENT DOCUMENTS

2011/0098481 A1\* 4/2011 Murata ................ C07D 405/06
548/252
2015/0175632 A1   6/2015 Ishibashi et al.

FOREIGN PATENT DOCUMENTS

CN    107324986 A  * 11/2017  ............. C07B 57/00
EP    2 545 917 A1     1/2013

OTHER PUBLICATIONS

CN107324986A—English Machine Translation (Year: 2017).*

(Continued)

*Primary Examiner* — Clinton A Brooks
*Assistant Examiner* — Josmalen M. Ramos-Lewis
(74) *Attorney, Agent, or Firm* — Birch, Stewart, Kolasch & Birch, LLP

(57) ABSTRACT

The present invention relates to a process for the preparation of a chiral prostaglandin enol intermediate of formula 1, comprising the steps of: separating a compound of formula 16-(R,S)-10 into its diastereomers by fractional crystallisation, reducing the 15-oxo group of the compound of formula 16-(R)-10, thereby obtaining a compound of formula 15-(R,S), 16-(R)-11, followed by removing the protecting group of the compound of formula 15-(R,S), 16-(R)-11, and isolating the compound of formula 1, and optionally, crystallizing the compound of formula 1. Optionally, the undesired isomer formed during fractional crystallization can be epimerized (Continued)

and further amount of the desired isomer can be recovered from the resulting mixture. The present invention also provides novel intermediates useful in the process. The invention further relates to a process for fractional crystallization of the compound of formula 16-(R,S)-10.

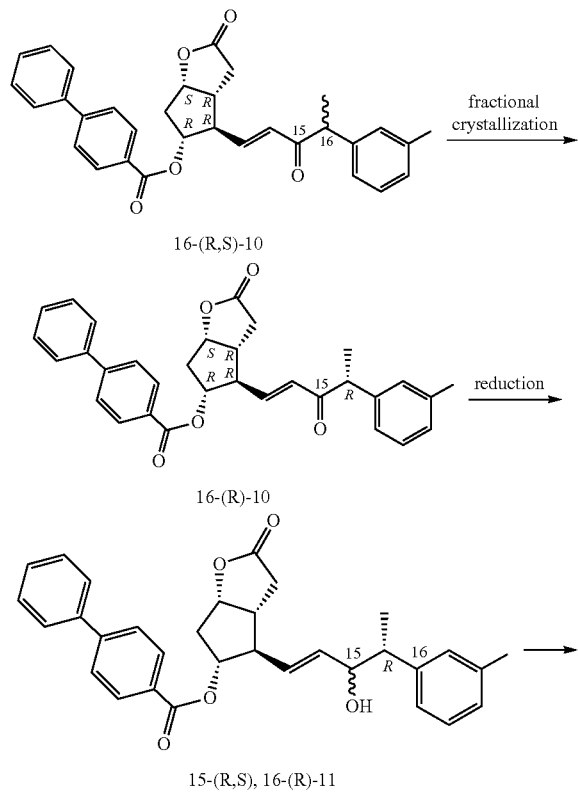

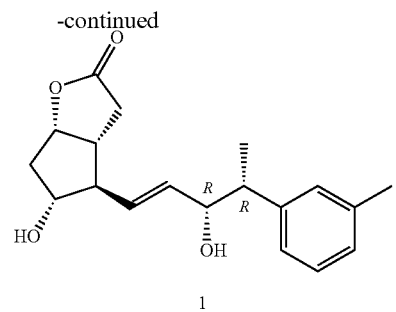

18 Claims, 10 Drawing Sheets

(56) References Cited

OTHER PUBLICATIONS

Hungarian Search Report for Hungarian Application No. 1900434, dated Feb. 19, 2020, with English translation.
International Search Report (Form PCT/ISA/210) for International Application No. PCT/HU2020/050058, dated Apr. 19, 2021.
Written Opinion of the International Searching Authority (Form PCT/ISA/237) for International Application No. PCT/HU2020/050058, dated Apr. 19, 2021.

* cited by examiner

PROCESS FOR THE PREPARATION OF A CHIRAL PROSTAGLANDIN ENOL INTERMEDIATE AND INTERMEDIATE COMPOUNDS USEFUL IN THE PROCESS

THE FILED OF THE INVENTION

The present invention relates to a process for the preparation of a chiral prostaglandin enol intermediate of formula 1. The invention further relates to intermediates used in this process and their preparation.

TECHNICAL BACKGROUND

The chiral enol of formula 1 is a potential key intermediate of effective prostaglandin and prostacyclin derivatives useful in human therapy.

The compound of formula 1 is named according to prostaglandin numbering: 16-methyl-17-(3-methylphenyl)-15-hydroxyenol.

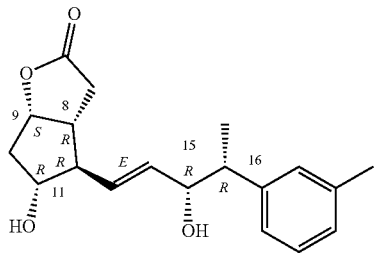

16-(R)-methyl-17-(3-methylphenyl)-15-(R)-hydroxyenol Numbering of the Compound According to Prostaglandin Numbering The name of the compound of formula 1 according to Chemical Abstracts: (3aR,4R,5R,6aS)-Hexahydro-5-hydroxy-4-[(1E,3R,4R)-3-hydroxy-4-(3-methylphenyl)-1-penten-1-yl]-2H-cyclopenta[b]furan-2-one.

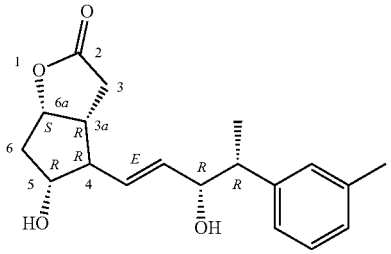

Numbering of the Compound According to the Chemical Abstracts Name

The preparation of the compound of formula 1 is described in WO 2010029925 A1, and WO 2011111714 A1. The compound of formula 1 is the intermediate of prostaglandin derivatives, which are claimed in said documents.

According to the known process described in the above documents (in the cited applications the same method is described for the preparation of the compound of formula 1), the optically active 2-(R)-(3-methylphenyl)propionic acid (2) was converted into methyl ester (3) with methanol and sulphuric acid, and by reacting the methyl ester (3) with dimethyl methylphosphonate (DMMP), a chiral phosphonate (4) was prepared. The chiral phosphonate (4) was reacted with benzoyl-Corey aldehyde (5) in a Horner-Wadsworth-Emmons (HWE) reaction, in the presence of sodium hydride base in dimethoxyethane (DME). The resulting protected enone (6) was reduced with (−)-B-chloro-diisopinocampheylborane, ((−)-DIP-Cl) in THF at −40° C. to benzoyl enol (7). The benzoyl enol was not purified. The benzoyl group was removed with methanolic potassium carbonate to give the chiral enol of formula 1, which was purified by chromatography on a silica gel column with hexane:ethyl acetate and ethyl acetate as eluents. No crystallization or state of the product has been described.

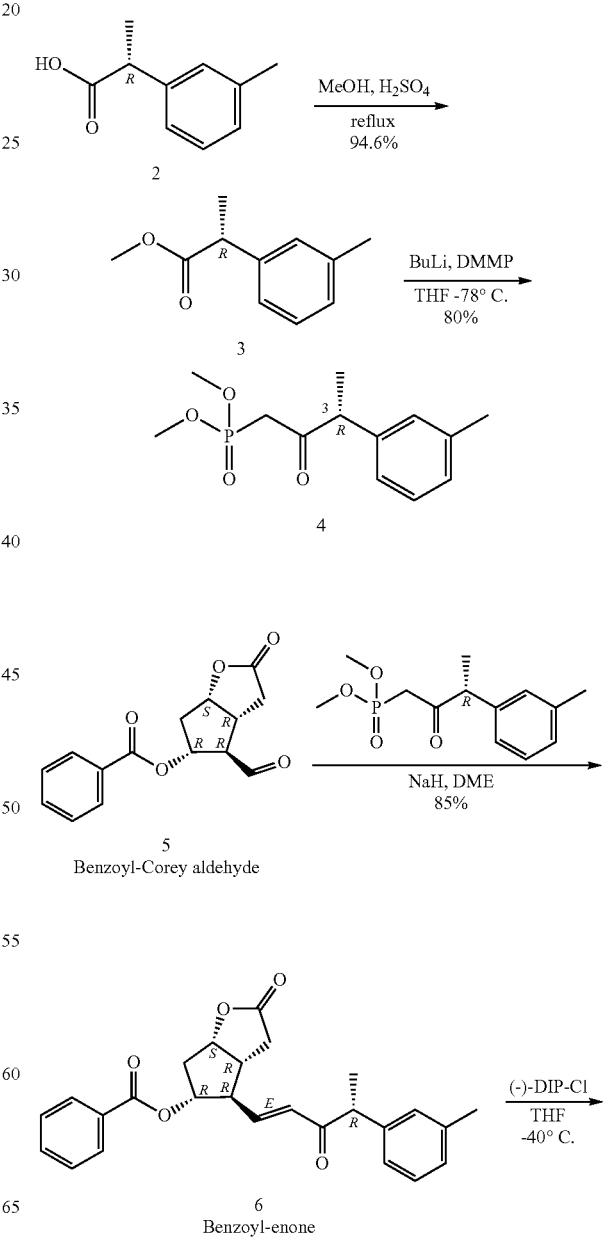

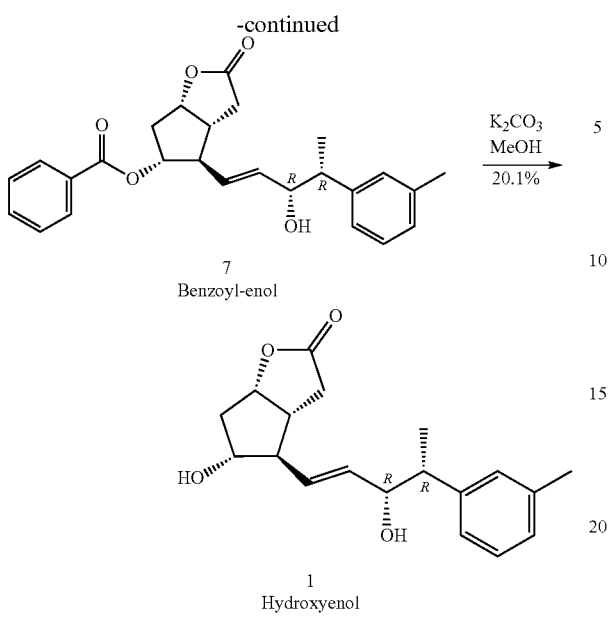

7
Benzoyl-enol

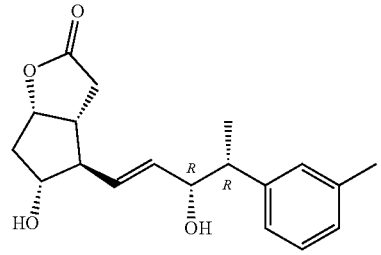

1
Hydroxyenol

The total yield of the known process using chiral starting materials is 17% calculated based on the benzoyl-Corey aldehyde (5).

The Problem to be Solved

The disadvantages of the known process are as follows:
the formation of the side chain is carried out with the expensive 3-(R)-optically active phosphonate (4); the starting material for the synthesis of phosphonate (4) is the expensive, chiral 2-(R)-(3-methylphenyl)propionic acid (2)
under the basic conditions of the HWE reaction (NaH, DME), the chiral side chain can easily racemize, resulting in a decrease in the optical purity of the 6 enone
the reduction of the 15-oxo group of the 6 enone is carried out with a large excess of an expensive chiral reagent ((-)-DIP-Cl), in a reaction with deep-freezing at −40° C.

Therefore, there is a need for a process to produce the compound of formula 1 more economically, using more readily available starting materials, with milder reaction conditions.

BRIEF DESCRIPTION OF THE INVENTION

We have developed a process in which
the benzoyl protecting group of the aldehyde (5) was replaced by p-phenylbenzoyl group, in order to facilitate the reduction of the 15-oxo group
we obtained a crystalline enone after the side chain was built, which allowed the separation of the enone diastereomers by fractional crystallization
the formation of the side chain is carried out with the cheap racemic phosphonate (3-(R,S)-4)
by using racemic phosphonate in the HWE reaction, we avoid the disadvantage of using chiral phosphonate which undergoes racemization in basic medium, reducing production yield and optical purity
the 15-oxo group of the enone can be reduced with a readily accessible reagent, so there is no need to use chemical reactions requiring energy-intensive deep-freezing.

A key element of our invention is providing a novel enone intermediate containing a racemic side chain (16-(R,S)-10), which is crystalline, and the accomplished separation of the enone diastereomers by fractional crystallization.

Accordingly, the present invention relates to a process for the preparation of a compound of formula 1,

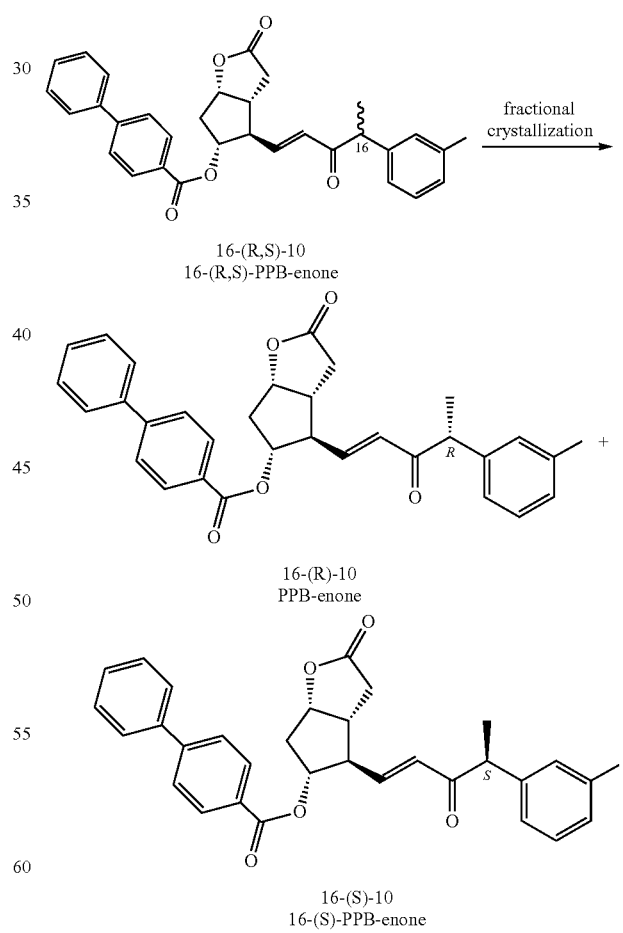

comprising the steps of:
separating a compound of formula 16-(R,S)-10 into its diastereomers 16-(R)-10 and 16-(S)-10 by fractional crystallisation, reducing the 15-oxo group of the compound of formula 16-(R)-10, thereby obtaining a compound of formula 15-(R,S), 16-(R)-11,

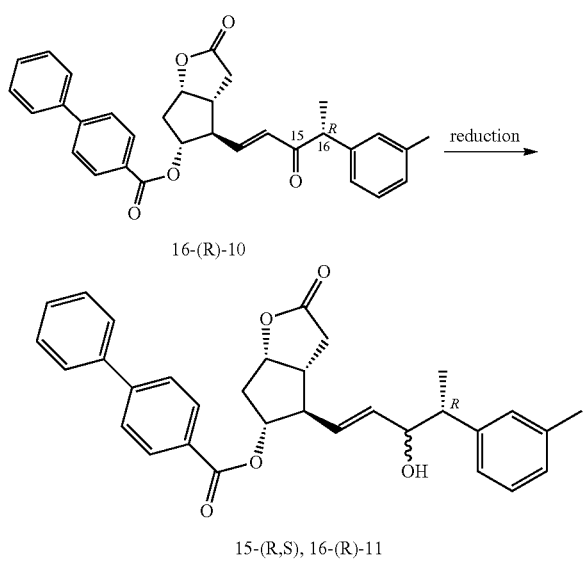

16-(R)-10 reduction 15-(R,S), 16-(R)-11 removing the protecting group of the compound of formula 15-(R,S), 16-(R)-11, isolating the compound of formula 1,

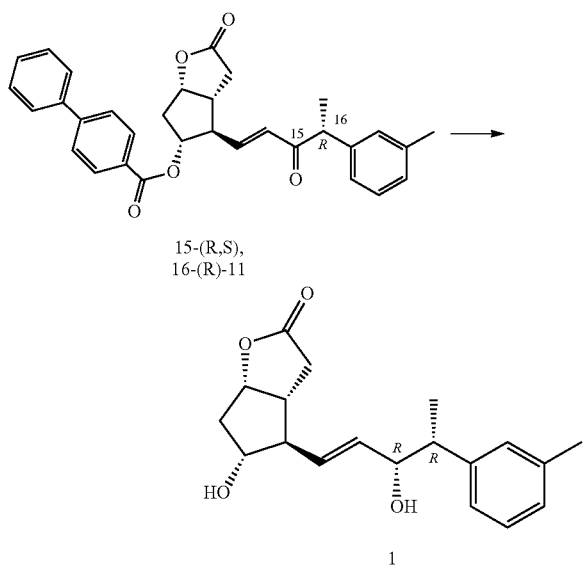

15-(R,S), 16-(R)-11

1 and optionally, crystallizing the compound of formula 1.

The solvent used for the fractional crystallization of the compound of formula 16-(R,S)-10 is preferably selected from $C_{1-3}$ alcohols, tert-butyl methyl ether and their mixtures. Preferred are methanol, tert-butyl methyl ether and their mixtures. Particularly preferred is tert-butyl methyl ether.

The fractional crystallization of the compound of formula 16-(R,S)-10 preferably comprises (a) suspending the compound of formula 16-(R,S)-10 in the solvent, refluxing the suspension, followed by cooling the mixture to 25-35° C. and stirring while maintaining the temperature, followed by filtering, washing and drying the precipitated crystals, thereby obtaining crystals $K_{r1}$;

(b) seeding the filtrate combined with the washing liquid with crystals of the compound of formula 16-(R)-10, cooling the suspension to 0-5° C. and stirring while maintaining the temperature, followed by filtering, washing and drying the precipitated crystals, thereby obtaining crystals $K_{r2}$; and optionally (c) suspending the previously filtered crystals $K_{r1}$ in the filtrate combined with the washing liquid, refluxing the suspension, followed by cooling the mixture to 25-35° C. and stirring while maintaining the temperature, followed by filtering, washing and drying the precipitated crystals, thereby obtaining crystals $K_{r3}$; and (d) seeding the filtrate combined with the washing liquid with crystals of the compound of formula 16-(R)-10, cooling to 0-5° C. and stirring while maintaining the temperature, followed by filtering, washing and drying the precipitated crystals, thereby obtaining crystals $K_{r4}$.

Compound of formula 16-(S)-10 is obtained as crystals $K_{r1}$ and $K_{r3}$ in step (a) and in optional step (c), and compound of formula 16-(R)-10 is obtained as crystals $K_{r2}$ and $K_{r4}$ in step (b) and in optional step (d).

Crystals $K_{r1}$ and $K_{r3}$ in step (a) and in optional step (c) contain predominantly the isomer 16-(S)-10. Therefore, crystals $K_{r1}$ and $K_{r3}$ are also called in the description as compound of formula 16-(S)-10 or 16-(S)-PPB-enone.

Crystals $K_{r2}$ and $K_{r4}$ in step (b) and in optional step (d) contain predominantly the isomer 16-(R)-10. Therefore, crystals $K_{r2}$ and $K_{r4}$ are also called in the description as compound of formula 16-(R)-10 or PPB-enone.

In step (a) and in optional step (c), after refluxing, the mixture is cooled to preferably 30-32° C. and is stirred at this temperature.

Stirring, in steps (a) and in optional step (c) at 25-35° C. (preferably at 30-32° C.), and in step (b) and optional step (d) at 0-5° C., is continued preferably for about 0.5-3 hours, more preferably for about 30-60 minutes.

In order to maximize the yield, optional steps (c) and (d) are preferably carried out as well.

The obtained crystals $K_{r2}$ and/or $K_{r4}$ are optionally recrystallized, preferably from a solvent selected from $C_{1-3}$ alcohols, tert-butyl methyl ether and their mixtures; or from a mixture of said solvents with dichloromethane. For recrystallization, particularly preferred is a mixture of methanol and dichloromethane, or a mixture of tert-butyl methyl ether and dichloromethane, wherein the ratio of dichloromethane is preferably at most 30 vol %; for example a methanol:dichloromethane 5:1 mixture or a tert-butyl methyl ether:dichloromethane 5:1 mixture.

Another important aspect of the invention is that we have found that the "wrong" 16-(S) isomer obtained by fractional crystallization can be easily epimerized. Therefore, in order to increase the yield, the obtained crystals $K_{r1}$ or $K_{r3}$ are preferably epimerized and the above-described fractional crystallization is repeated.

Epimerization can be carried out under either acidic or basic conditions. Epimerization can be carried out for example in ethyl acetate in the presence of silica gel with triethyl amine, or in ethyl acetate in the presence of aluminium oxide, or in toluene with para-toluenesulfonic acid.

Preferably, the epimerization is carried out in toluene with para-toluenesulfonic acid at about 65-75° C. by stirring during about 15-20 hours, or in ethyl acetate in the presence of silica gel with triethyl amine at about 55-65° C. by stirring during about 10-14 hours.

The 15-oxo group of the compound of formula 16-(R)-10 can be reduced using methods known in the art, preferably with an aqueous solution of sodium borohydride in the presence of silica gel.

The protecting group of the compound of formula 15-(R,S)-16-(R)-11 can be removed using known methods, for example, by methanolysis in the presence of potassium carbonate, or by using NaOMe/methanol, NaOH or other base in a suitable aqueous-organic solvent mixture, or by a mineral acid in alcohol, etc.

After deprotection, the desired product is isolated. Isolation may be carried out using known methods, such as crystallization or chromatography, or combinations thereof. Preferably, chromatography is applied, by which method the desired 15-epimer can be separated from the undesired one and from other impurities in a single step. Chromatography may be carried out for example on silica gel column with dichloromethane:acetone eluent, preferably with dichloromethane:acetone=7:1 followed by 2:1 mixture.

The fractions containing the product are preferably combined and evaporated, thereby the product is obtained in the form of an oil. Optionally, the evaporation residue is crystallized, thereby obtaining crystalline hydroxyenol of formula 1. Hydroxyenol is preferably crystallized from an ether-type solvent or solvent mixture, for example from a mixture of tert-butyl methyl ether and diisopropyl ether.

The compound of formula 16-(R,S)-10 is preferably prepared by reacting an aldehyde of formula 9 with a racemic phosphonate of formula 3-(R,S)-4:

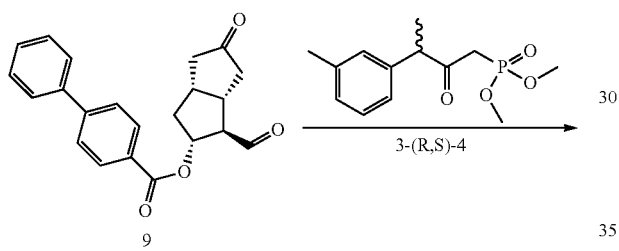

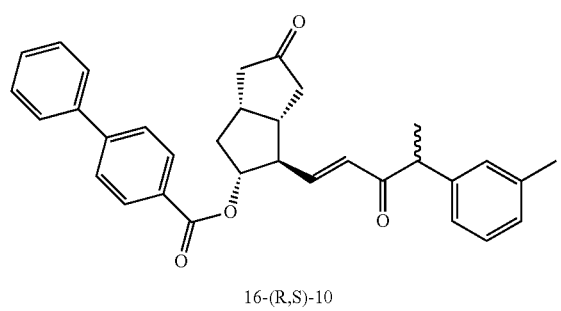

16-(R,S)-10

The above reaction, known in the literature as Horner-Wadsworth-Emmons (HWE) reaction, may be carried out using various bases; preferably with potassium hydroxide base at about 20-25° C., or with sodium hydride at about 0-10° C.

One of the starting materials of the HWE reaction, the aldehyde of formula 9 is preferably prepared by oxidizing PPB-Corey lactone of formula 8:

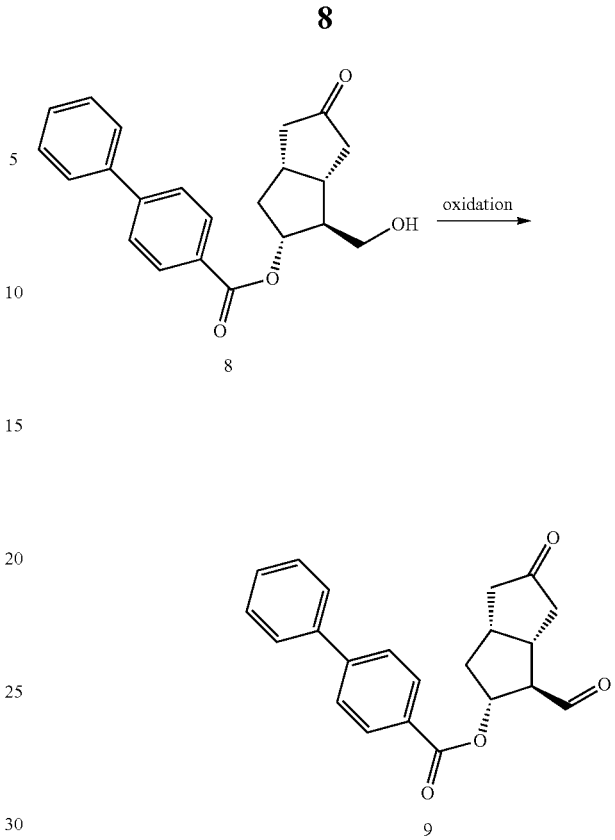

in a manner known in the art, for example with dimethyl sulphoxide in the presence of phosphoric acid and e.g. dicyclohexylcarbodiimide, or with sodium hypochlorite in the presence of a catalyst containing a nitroxyl radical, preferably with sodium hypochlorite in the presence of a catalyst containing a nitroxyl radical.

Compound of formula 8 (PPB-Corey lactone) is a readily accessible compound, available in high quantities in the prostaglandin chemistry, as it is a starting material for a large number of prostaglandin derivatives.

The other starting material of the HWE reaction is the racemic phosphonate (3-(R,S)-4). The optically active phosphonate of formula 4 and the racemic phosphonate of formula (3-(R,S)-4) are known compounds (WO 2011111714 A1, WO 2010029925 A1). The chiral phosphonate can be prepared from the expensive chiral carboxylic acid (the study published in *J. Chem. Soc., Perkin Trans. 2*, 1998, pp 1767-1775 underlines the difficulty of obtaining the starting chiral carboxylic acid itself) by an expensive process, whereas the racemic compound can be prepared from the inexpensive racemic carboxylic acid by an inexpensive process.

Provided are two process variants for the preparation of the racemic compound, which are suitable for industrial scale production.

Accordingly, the racemic phosphonate of formula (3-(R,S)-4) is advantageously prepared by the following reaction scheme, according to variant A) or B):

A.)

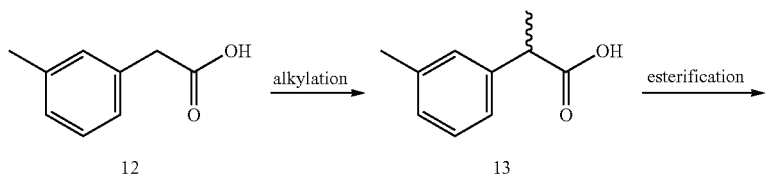

B.)

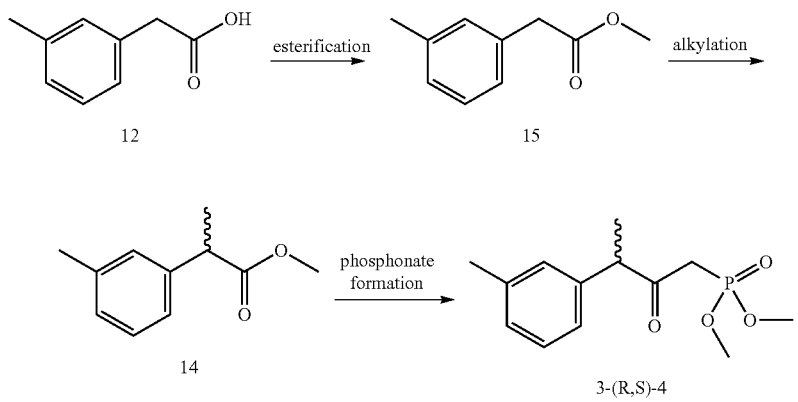

wherein, variant A) comprises:

alkylating methylphenylacetic acid of formula 12, preferably with methyl iodide in the presence of a strong base, such as butyl lithium or lithium diisopropylamide;

converting the resulting methylphenylpropionic acid of formula 13 into a methyl ester of formula 14 using methanol in the presence of an acid, such as hydrochloric acid or sulphuric acid;

followed by reacting the methyl ester of formula 14 with dimethyl methylphosphonate (DMMP) in the presence of a strong base, such as butyl lithium or lithium diisopropylamide, thereby obtaining racemic phosphonate of formula 3-(R,S)-4;

and variant B) comprises:

converting methylphenylacetic acid of formula 12 into methylphenylacetic acid methyl ester of formula 15 using methanol in the presence of an acid, such as hydrochloric acid or sulphuric acid;

alkylating the methylphenylacetic acid methyl ester of formula 15, preferably with methyl iodide in the presence of a strong base, such as butyl lithium or lithium diisopropylamide, thereby obtaining methyl ester of formula 14;

followed by reacting the methyl ester of formula 14 with dimethyl methylphosphonate (DMMP) in the presence of a strong base, such as butyl lithium or lithium diisopropylamide, thereby obtaining racemic phosphonate of formula 3-(R,S)-4.

Further objects of the invention are the following new intermediate compounds:

a compound of formula 16-(R,S)-10:

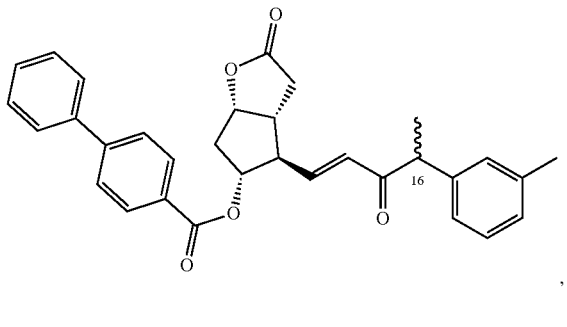

16-(R,S)-10 a compound of formula 16-(R)-10:

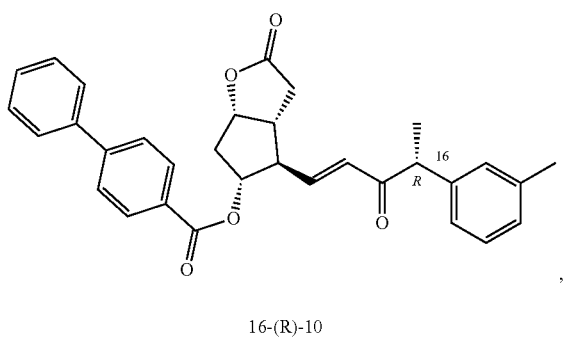

16-(R)-10 a compound of formula 16-(S)-10:

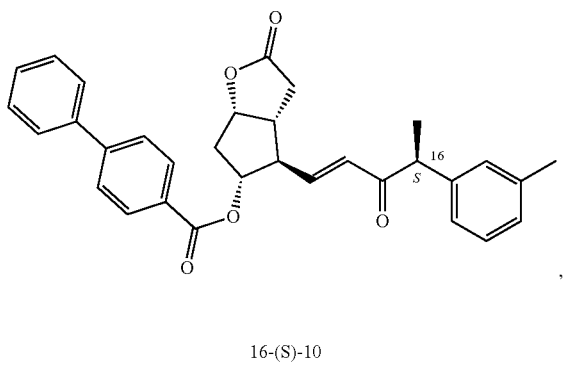

16-(S)-10 and a compound of formula 15-(R,S), 16-(R)-11:

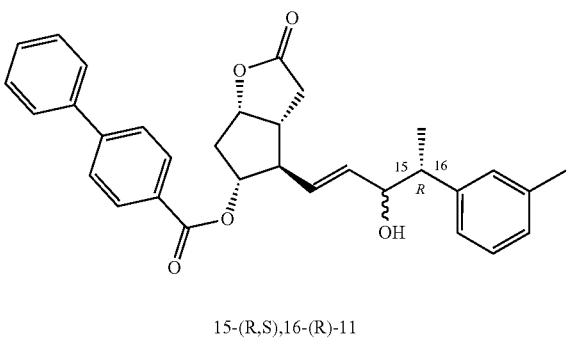

15-(R,S),16-(R)-11

These compounds are useful as intermediates for the preparation of prostaglandin and prostacyclin derivatives.

A further object of the invention is a process for the fractional crystallization of the compound of formula 16-(R,S)-10, using a solvent selected from $C_{1-3}$ alcohols, tert-butyl methyl ether and their mixtures, preferably selected from methanol, tert-butyl methyl ether and their mixtures; preferably comprising (a) suspending the compound of formula 16-(R,S)-10 in the solvent, refluxing the suspension, then cooling the mixture to 25-35° C. and stirring while maintaining the temperature, followed by filtering, washing and drying the precipitated crystals, thereby obtaining crystals $K_{r1}$;

(b) seeding the filtrate combined with the washing liquid with crystals of the compound of formula 16-(R)-10, cooling the suspension to 0-5° C. and stirring while maintaining the temperature, followed by filtering, washing and drying the precipitated crystals, thereby obtaining crystals $K_{r2}$; and optionally (c) suspending the previously filtered crystals $K_{r1}$ in the filtrate combined with the washing liquid, refluxing the suspension, then cooling the mixture to 25-35° C. and stirring while maintaining the temperature, followed by filtering, washing and drying the precipitated crystals, thereby obtaining crystals $K_{r3}$; and (d) seeding the filtrate combined with the washing liquid with crystals of the compound of formula 16-(R)-10, cooling to 0-5° C. and stirring while maintaining the temperature, followed by filtering, washing and drying the precipitated crystals, thereby obtaining crystals $K_{r4}$, wherein compound of formula 16-(S)-10 is obtained as crystals $K_{r1}$ and $K_{r3}$ in step (a) and in optional step (c), and compound of formula 16-(R)-10 is obtained as crystals $K_{r2}$ and $K_{r4}$ in step (b) and in optional step (d).

Both isomers can be further purified by recrystallization, preferably from a solvent selected from $C_{1-3}$ alcohols, tert-butyl methyl ether and their mixtures; or from a mixture of said solvents with dichloromethane; preferably from a mixture of methanol and dichloromethane, or from a mixture of tert-butyl methyl ether and dichloromethane.

A further object of the invention is a process for the preparation of the compound of formula 16-(S)-10, comprising (a) suspending a compound of formula 16-(R,S)-10 in a solvent selected from $C_{1-3}$ alcohols, tert-butyl methyl ether and their mixtures, preferably selected from methanol, tert-butyl methyl ether and their mixtures, refluxing the suspension, followed by cooling the mixture to 25-35° C. and stirring while maintaining the temperature, followed by filtering, washing and drying the precipitated crystals, thereby obtaining crystals $K_{r1}$;

and optionally (b) seeding the filtrate combined with the washing liquid with crystals of the compound of formula 16-(R)-10, cooling the suspension to 0-5° C. and stirring while maintaining the temperature, followed by filtering the precipitated crystals; and (c) suspending the previously filtered crystals $K_{r1}$ in the filtrate, refluxing the suspension, followed by cooling the mixture to 25-35° C. and stirring while maintaining the temperature, followed by filtering, washing and drying the precipitated crystals, thereby obtaining crystals $K_{r3}$;

and optionally, recrystallizing the obtained crystals $K_{r1}$ or $K_{r3}$ from a mixture of dichloromethane and a solvent selected from $C_{1-3}$ alcohols, tert-butyl methyl ether and their mixtures; preferably from a mixture of methanol and dichloromethane, or from a mixture of tert-butyl methyl ether and dichloromethane, thereby obtaining the compound of formula 16-(S)-10.

Another object of the invention is a crystalline form of a compound of formula 1,

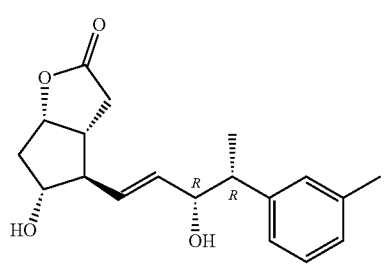

having main peaks in its powder X-ray diffraction pattern obtained using copper anode at 6.2; 11.4; 14.5; 15.6; 17.4; 18.1; 18.6; 20.4; 23.2 and 24.9±0.2 degree 2-theta.

BRIEF DESCRIPTION OF THE DRAWINGS

FIG. 3 shows a DSC curve of 16-(R)-PPB-enone prepared according to Example 3.a.

FIG. 4 shows a powder X-ray diffraction pattern of 16-(R)-PPB-enone prepared according to Example 3.a.

TERMS AND ABBREVIATIONS USED IN THE DESCRIPTION

Figure 1:
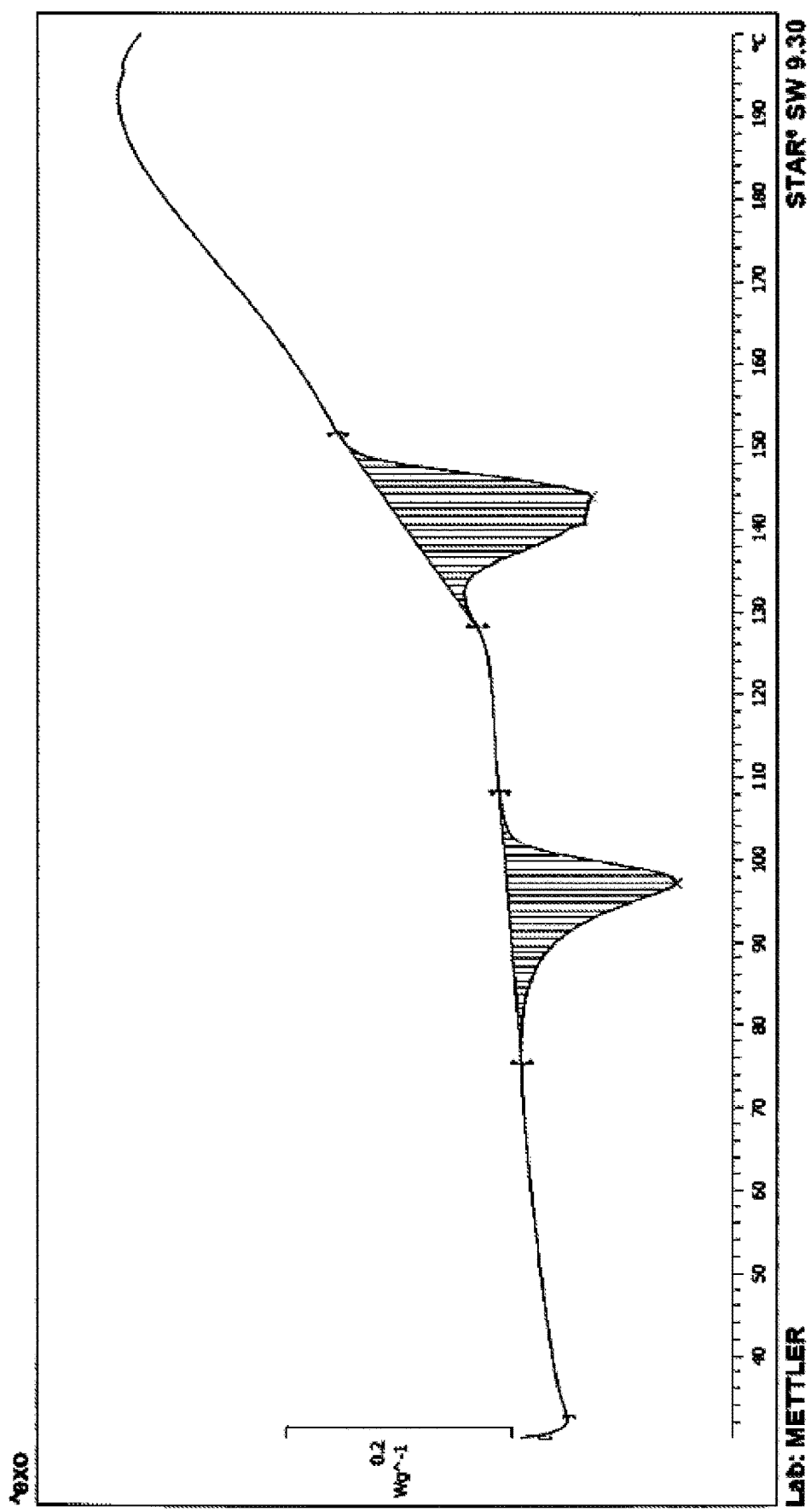
FIG. 1 shows a DSC curve of 16-(R,S)-PPB-enone prepared according to Example 1.

As used herein, in connection with an asymmetric carbon atom,
- the R symbol means that the connection order of substituents according to the Cahn-Ingold-Prelog rules is clockwise,
- the S symbol means that the connection order of substituents according to the Cahn-Ingold-Prelog rules is anti-clockwise,
- the R,S symbol means that the connection order of substituents according to the Cahn-Ingold-Prelog rules is clockwise and anti-clockwise in the same proportion.

Enantiomers are those stereoisomeric molecules, in which all asymmetric carbon atoms have the opposite configuration of (i.e., they are mirror images of one another).

Diastereomers are those stereoisomeric molecules, which are not in mirror image relationship to one another.

Epimers are those diastereomers, which differ only in the configuration of a single chiral centre.

In the description, when ratios are given in connection with liquids, they are meant to be volume/volume ratios.

DETAILED DESCRIPTION OF THE INVENTION

Preferably, the starting material of the complete process is Corey lactone containing PPB protecting group (8), which is oxidized in the first reaction step to aldehyde (9), and the 9 aldehyde is reacted with 3-(R,S)-4 racemic phosphonate in a Horner-Wadsworth-Emmons (HWE) reaction.

The starting material of the process may be directly the aldehyde of formula 9. However, as aldehydes are less stable, PPB-Corey lactone 8 is more readily available and is easier to store, so the use of the latter is more convenient.

The obtained enone diastereomers (16-(R,S)-10) are separated by fractional crystallization.

The undesired, "wrong" isomer (16-(S)-10) can be epimerized in acidic or basic medium. After reaching an isomer ratio 16-(R)-10:16-(S)-10 of about 1:1, further amount of the desired isomer, PPB-enone can be obtained by fractional crystallization.

The crystals of PPB-enone are combined, the 15-oxo group is reduced to hydroxyl group. After removing the protective group of the p-phenylbenzoyl-protected enol (15-(R,S), 16-(R)-11), the desired compound of formula 1 is isolated.

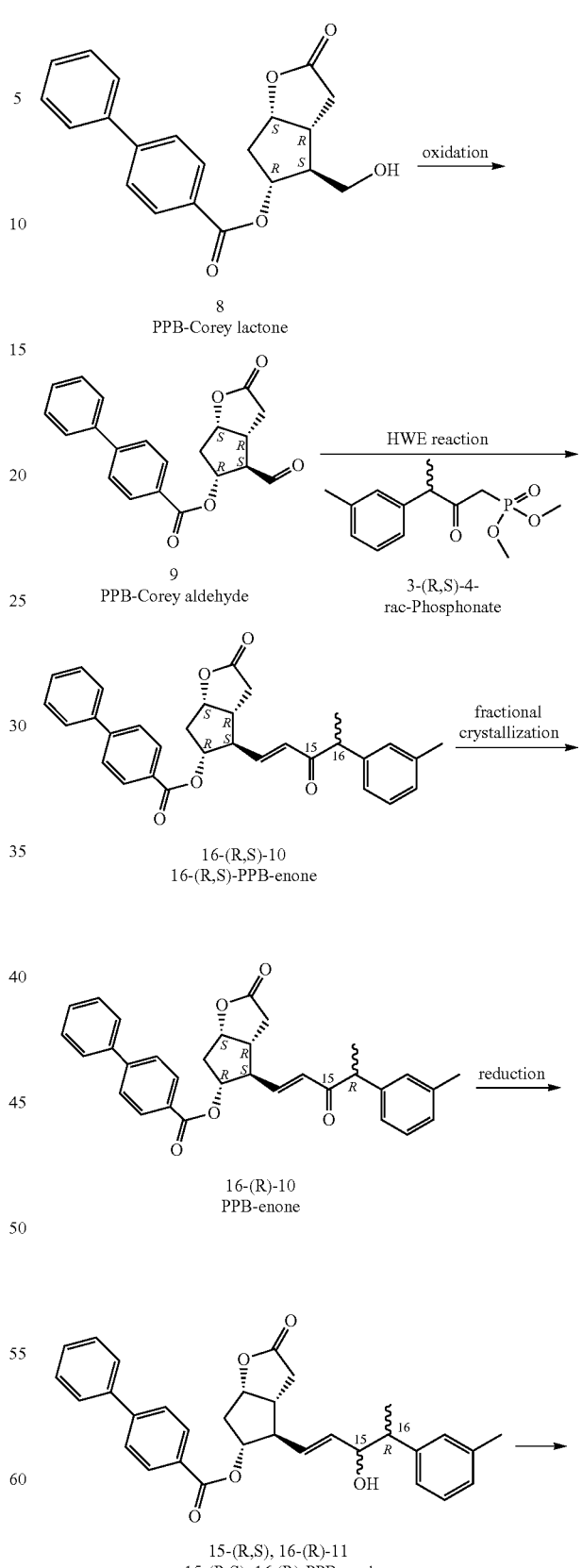

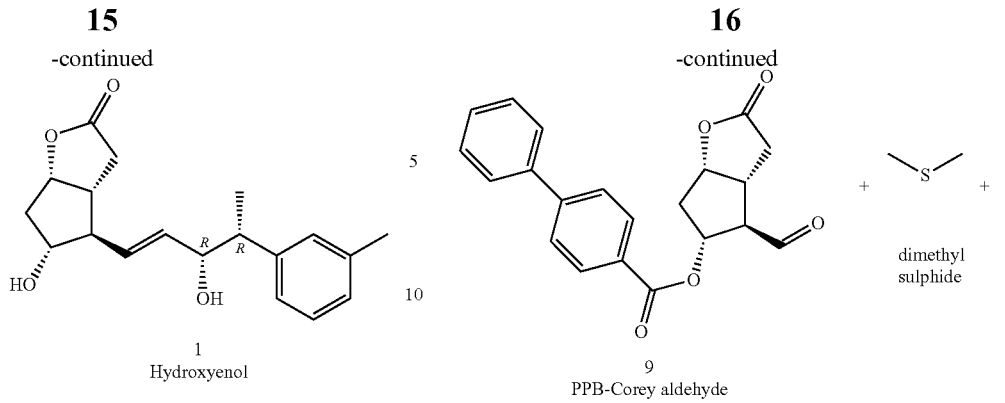

1
Hydroxyenol

The individual steps of the whole process, starting from PPB-Corey lactone, are detailed below.

Step 1: Oxidation

The primary hydroxyl group of the PPB-protected Corey lactone (8) can be oxidized by any known oxidation method that selectively converts the primary hydroxyl group to aldehyde. Oxidation methods may involve for example

- chromium-containing oxidants such as Collins reagent (chromium trioxide—pyridine complex, $CrO_3.Py_2$), pyridinium dichromate, or pyridinium chlorochromate
- hypervalent iodine reagent such as Dess-Martin oxidation
- activated dimethyl sulphoxide (DMSO), such as Swern oxidation, Pfitzner-Moffatt oxidation
- sodium hypochlorite (aqueous solution or crystalline pentahydrate) in the presence of a catalyst containing a nitroxyl radical [such as TEMPO (2,2,6,6-tetramethylpiperidine-1-oxyl) or AZADO (2-azaadamantane-N-oxyl)].

The oxidation of PPB-Corey lactone was performed with Pfitzner-Moffatt oxidation system comprising activated dimethyl sulphoxide—DCC (dicyclohexylcarbodiimide) and Anelli oxidation using sodium hypochlorite—TEMPO oxidizing agent.

Pfitzner-Moffatt oxidation (*J. Am. Chem. Soc.*, 1963, 85, 3027-3028):

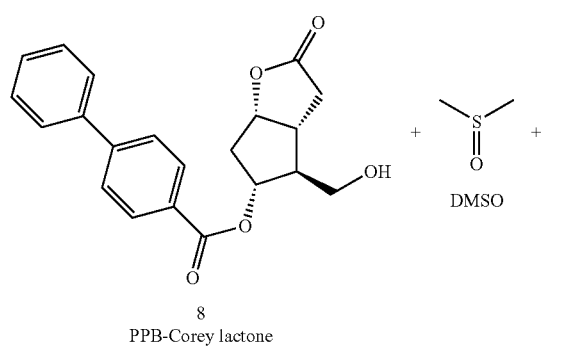

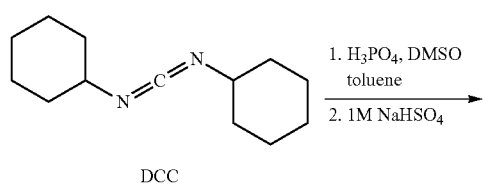

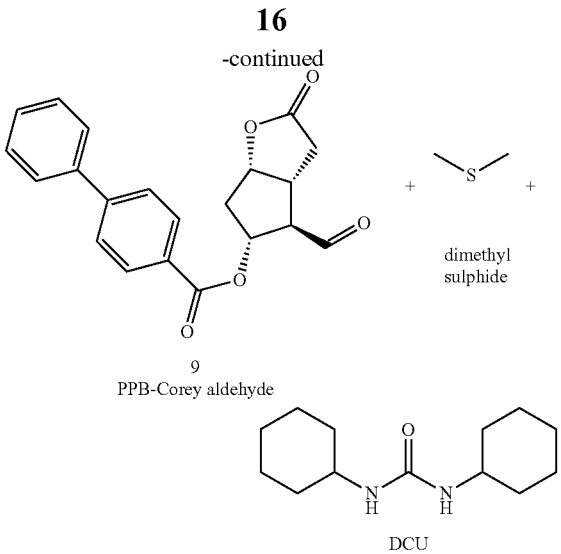

9
PPB-Corey aldehyde

Anelli oxidation (*J. Org. Chem.*, 1987, 52, 2559-2562):

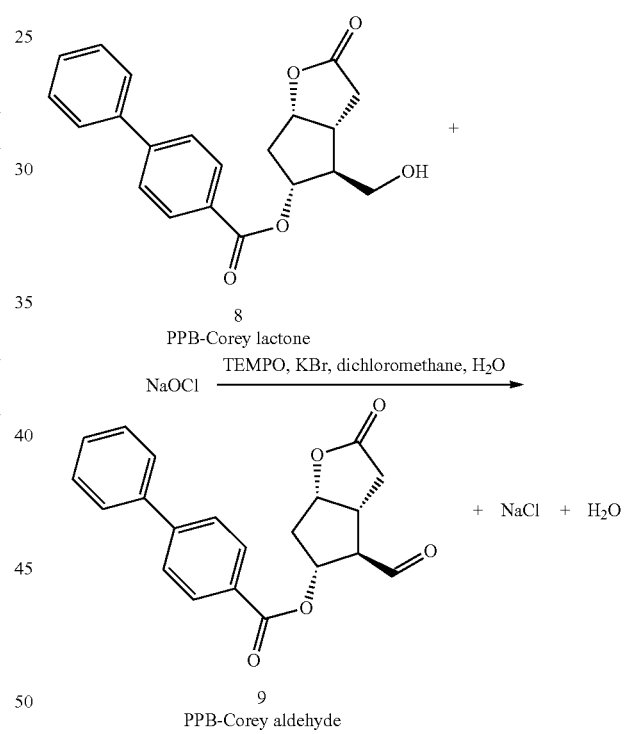

9
PPB-Corey aldehyde

Both oxidations are suitable for the preparation of PPB-Corey aldehyde (9). It is not necessary to isolate the aldehyde prior to the Horner-Wadsworth-Emmons (HWE) reaction.

However, the Anelli oxidation is considered more preferable, because the Pfitzner-Moffatt oxidation produces very unpleasant by-products, the dimethyl sulphide, which has disagreeable odour, and DCU (dicyclohexyl urea). Removal of DCU requires expensive and time-consuming column chromatography when purifying the PPB-enone, since well-crystallizing DCU would contaminate the crystalline PPB-enone.

After oxidation, it is not necessary to isolate the sensitive aldehyde from the reaction mixture; preferably, the resulting reaction mixture is taken to the next reaction step.

Step 2: HWE Reaction

The Corey aldehyde containing the p-phenylbenzoyl protecting group (9) was reacted with racemic phosphonate (3-(R,S)-4) using HWE reaction (R. Bruckner, Organic Mechanism, Edited by M. Harmata, Springer-Verlag Berlin Heidelberg 2010). There are several bases available in the literature for the formation of phosphonate anions; of these, sodium hydride and potassium hydroxide were chosen for our experiments.

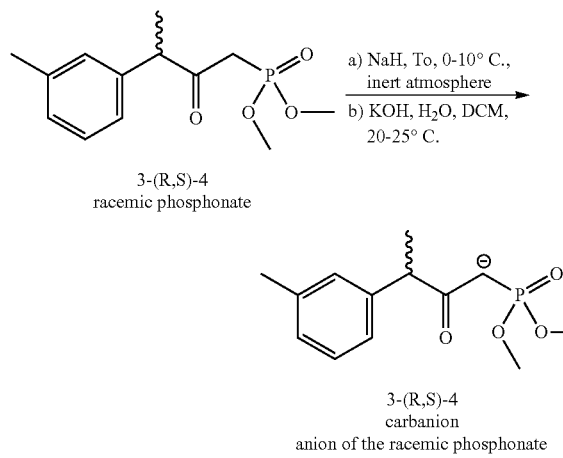

3-(R,S)-4
racemic phosphonate a) NaH, To, 0-10° C., inert atmosphere
b) KOH, H$_2$O, DCM, 20-25° C.

3-(R,S)-4
carbanion
anion of the racemic phosphonate

The formation of phosphonate anion was appropriate with both bases, since in both cases the HWE reaction between the phosphonate anion and the PPB-Corey aldehyde (9) was complete. However, from the viewpoint of scaling-up, the use of a potassium hydroxide solution is preferred.

The potassium hydroxide solution is much easier to handle than the sodium hydride dispersion, which is sensitive to air humidity, so there is no need for an anhydrous medium, and the anion formation and the HWE reaction requires less cooling energy than in case of using NaH base.

The yield of 16-(R,S)-PPB-enone (16-(R,S)-10) was highest when oxidation was carried out by the Anelli method, and potassium hydroxide solution was used to form the phosphonate anion. In this case, the yield of 16-(R,S)-PPB-enone, crystallized from isopropanol was 85%. The product contains PPB-enone (16-(R)-10) ("good") and its epimer, 16-(S)-PPB-enone (16-(S)-10) ("wrong") isomers in a 1:1 ratio.

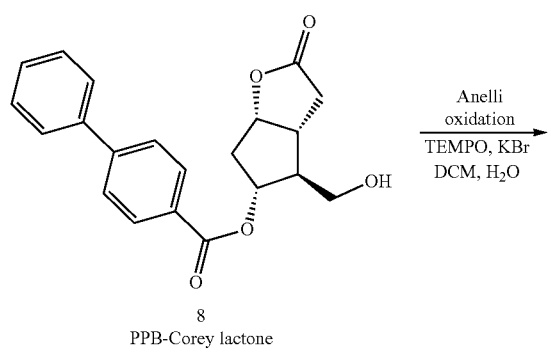

8
PPB-Corey lactone

Anelli oxidation
TEMPO, KBr
DCM, H$_2$O

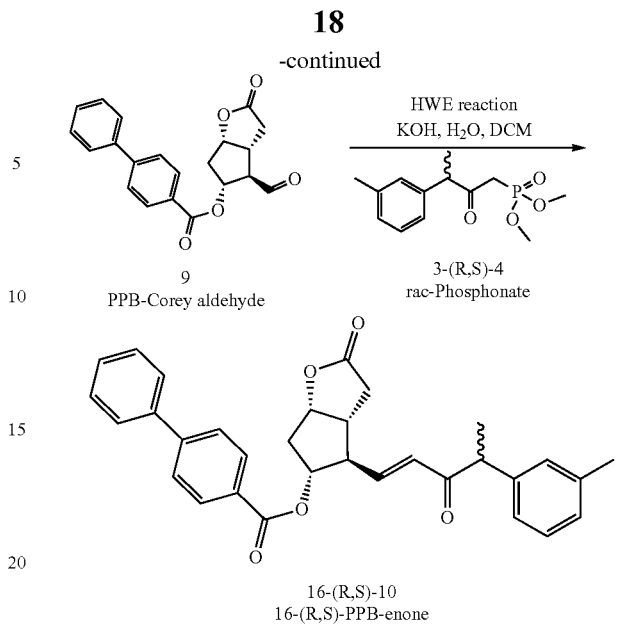

9
PPB-Corey aldehyde

HWE reaction
KOH, H$_2$O, DCM 3-(R,S)-4
rac-Phosphonate 16-(R,S)-10
16-(R,S)-PPB-enone Step 3: Fractional Crystallization It is well known in the chemical literature that the physical properties of diastereomers are different (e.g., https://en.wikipedia.org/wiki/Diastereomer, downloaded on 20. 05. 2019). Thus, in the early stages of development, we tried to separate the PPB-enone diastereomers by column chromatography. Although we have not found an effective, industrially applicable chromatographic separation with good yield, we obtained pure epimers by this technique. Both isomers (16-(R)-10 and 16-(S)-10) obtained after chromatographic separation were crystalline.

Thereafter several solvents for fractional crystallization of the diastereomers were tried and it was found that $C_{1-3}$ alcohols and tert-butyl methyl ether are suitable for this purpose.

The solubility (g/100 ml) of the PPB-enone isomers in some of the solvents with which crystallization was attempted is shown below:

| Isomer Temperature | 16-(R)-PPB-enone | | 16-(S)-PPB-enone | | 16-(R,S)-PPB-enone | |
|---|---|---|---|---|---|---|
| | 23° C. | Reflux | 23° C. | Reflux | 23° C. | Reflux |
| iPrOH | 0.18 | 2.22 | insoluble | 0.29 | insoluble | 0.80 |
| EtOH | 0.43 | 4.00 | insoluble | 0.33 | insoluble | 0.77 |
| MeOH | 0.45 | 5.00 | insoluble | 0.33 | insoluble | 0.91 |
| DIPE | insoluble | insoluble | insoluble | 0.2 | insoluble | insoluble |
| TBME | 0.71 | 8.00 | insoluble | 0.13 | 0.14 | 0.33 |

Based on the solubility data, fractional crystallization in $C_{1-3}$ alcohols and tert-butyl methyl ether (TBME) can be performed in relatively good yields (however, it should be noted that diisopropyl ether (DIPE), which is also ether-type, was not suitable in terms of solubility). Particularly preferred are methanol and tert-butyl methyl ether and mixtures of these solvents.

Upon repeating the crystallization procedure several times, it was found that, in case of methanol, the first generation product crystallizes with a few percent higher 16-(S)-PPB-enone content in some batches. Experiments have shown that the use of TBME makes the technology more robust, and, contrary to methanol, anomaly has not been observed. A further advantage is that the "good" isomer is slightly more soluble in TBME than in methanol, while the 16-(S) derivative is equally insoluble in both solvents at room temperature. This may be the reason that we get a much cleaner product. Already in the first generation, the 16-(S) impurity is only about 2.5%, which after recrystallization decreases to about 0.5%. This is very advantageous, as the total amount of impurities in the final product may not exceed 1.5%. Thus, less crystallization steps result in a purer product.

In addition, the removal of the 16-(S) impurity from the final product is much more difficult, requiring multiple recrystallization of hydroxyenol (1), so it is particularly advantageous to obtain a purer product in the beginning.

Comparison of fractional crystallization in TBME and methanol:

| Isomer ratio (HPLC area %) | TBME 16-(R)-PPB-enone: 16-(S)-PPB-enone | MeOH 16-(R)-PPB-enone: 16-(S)-PPB-enone |
|---|---|---|
| First generation ($K_{r2}$) | 98.07:1.93 | 93.52:6.48 |
| Second generation ($K_{r4}$) | 97.45:2.55 | 93.79:6.21 |
| 1. Recrystallization | 99.60:0.40 | 96.66:3.34 |
| 2. Recrystallization | not necessary | 97.89:2.11 |
| Yield (%) based on 16-(R)-PPB-enone | 60 | 58 |
| Yield (%) based on 16-(R,S)-PPB-enone | 30 | 29 |

Based on the above, for the fractional crystallization, especially on an industrial scale, tert-butyl methyl ether is a particularly preferred solvent.

Both in alcohols and in TBME, the less soluble 16-(S)-PPB-enone (16-(S)-10) precipitates first during fractional crystallization, at about 30° C.

The fractional crystallization is preferably carried out by refluxing the 16-(R,S)-PPB-enone in tert-butyl methyl ether or in $C_{1-3}$ alcohols, or in a mixture thereof, preferably for about 15-60 minutes, and then the reaction mixture is cooled to about 25-35° C., preferably to about 30-32° C., and stirred for a further 0.5-3 hours, preferably for about 30 minutes, while maintaining the temperature.

The precipitated crystals of 16-(S)-PPB-enone ($K_{r1}$) are filtered, the filtrate is seeded with the PPB-enone seed crystal, cooled to about 0-5° C. and the desired isomer (16-(R)-isomer) is crystallized ($K_{r2}$) over 0.5-3 hours, preferably over about 1 hour.

The PPB-enone seed crystals were obtained by column chromatography of the diastereomeric mixture on a silica gel column with chloroform:tert-butyl methyl ether as eluent.

Preferably, additional 16-(R)-isomer, PPB-enone, can be recovered from the crystallization mixture by adding the filtered $K_{r1}$ crystals to the mother liquor, reheating the suspension to reflux, and repeating the crystallization process. The 16-(S)-PPB-enone ($K_{r3}$) is crystallized at about 25-35° C., afterwards the mother liquor is seeded with PPB-enone crystals, cooled to 0-5° C., and a second generation of PPB-enone crystals is obtained ($K_{r4}$).

Based on the experimental data, the use of methanol or a methanol-containing crystallization solvent mixture requires more recrystallizations to produce the product with the desired epimeric purity.

Yield of fractional crystallization from TBME, based on data of the following specific examples:

Yield of PPB-enone ($K_{r2}$ and $K_{r4}$ together): calculated based on the starting 16-(R,S)-PPB-enone (16-(R,S)-10): 31%, based on the PPB-enone (16-(R)-10) contained therein: 62%.

The combined $K_{r2}$ and $K_{r4}$ crystals can be recrystallized from a TBME:dichloromethane mixture. The yield of recrystallization is 98%.

Yield of 16-(S)-PPB-enone (amount of $K_{r3}$): calculated based on the starting 16-(R,S)-PPB-enone (16-(R,S)-10): 48.5%.

Epimerization

A further advantage of our process is that the "wrong" isomer, 16-(S)-PPB-enone (16-(S)-10) can be epimerized both in basic and in acidic media.

Regarding epimerization, it is noted that since the molecule is sensitive to bases and acids as well (degradation/elimination can be expected), it was surprisingly found that the compound can be epimerized with an acceptable yield. This is true for both acidic and basic conditions. The epimerization equilibrium is at an isomer ratio of approximately 1:1. From the reaction mixture, containing the PPB-enone diastereomers in a ratio of 1:1, additional PPB-enone can be obtained by fractional crystallization. The yield increase, which can be reached in this way by one epimerization, is approximately 12-17% calculated based on 16-(R,S)-PPB-enone (24-34% based on 16-(S)-PPB-enone), depending on the conditions used.

Repeated epimerization of 16-(S)-PPB-enone could significantly increase the yield of PPB-enone (theoretically up to almost 100%), but the by-products formed during epimerization considerably reduce the maximum yield of PPB-enone. In our experience, repeating the epimerization does not result in a notable increase in yield.

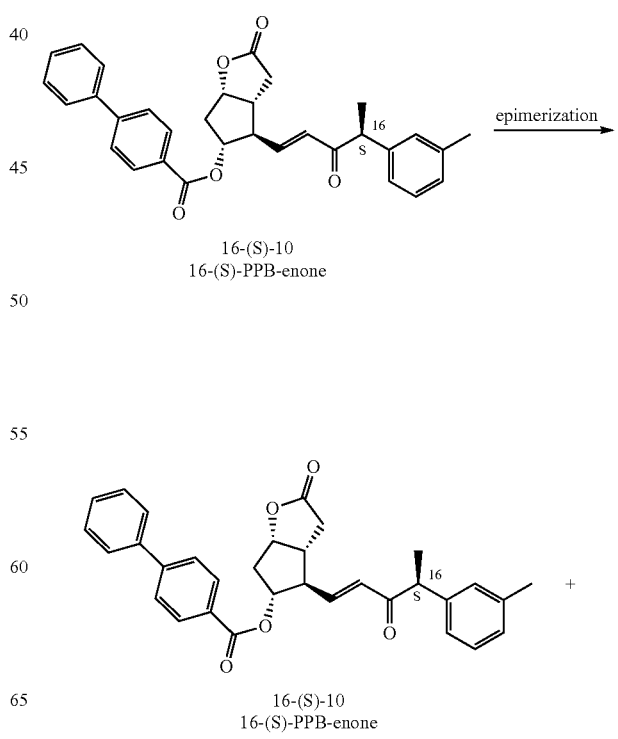

16-(S)-10
16-(S)-PPB-enone 16-(S)-10
16-(S)-PPB-enone

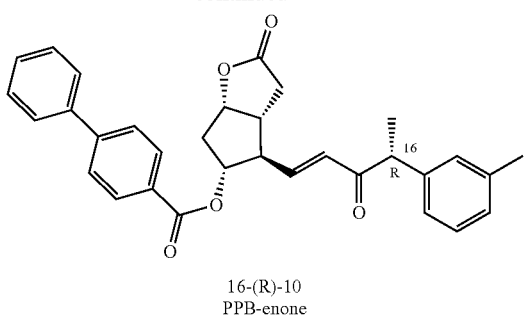

16-(R)-10
PPB-enone

Taking into account the PPB-enone crystals obtained via epimerization, the yield of PPB-enone is 47% (calculated based on 16-(R,S)-PPB-enone).

The combined PPB-enone crystals can be recrystallized with a yield of 98% from dichloromethane:TBME mixture to further increase their purity, if needed.

Step 4: Reduction

The next step is the reduction of the 15-oxo group of PPB-enone (16-(R)-10). During the reduction, beside the expected product, PPB-enol (15-(R), 16-(R)-11), the epimeric impurity, 15-(S)-PPB-enol (15-(S), 16-(R)-11) is also formed.

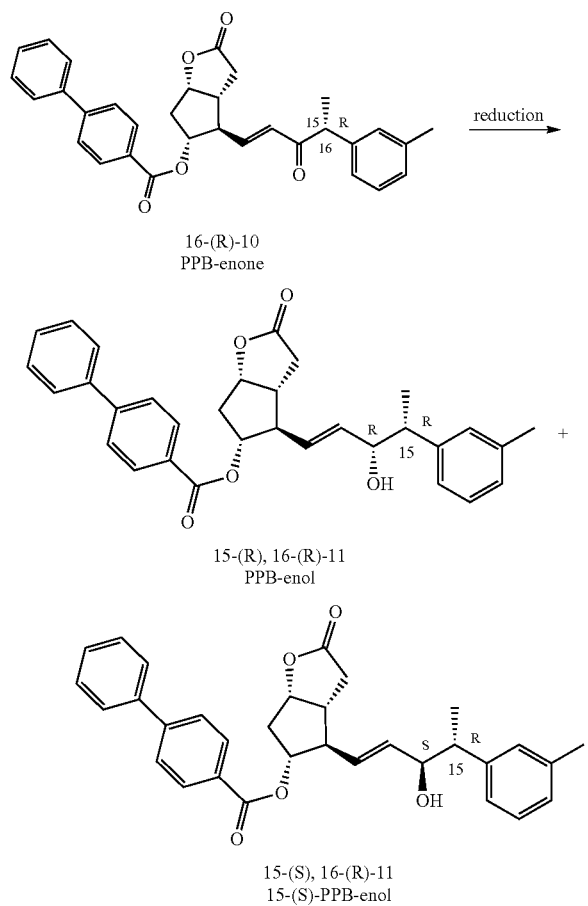

16-(R)-10
PPB-enone reduction 15-(R), 16-(R)-11
PPB-enol

+

15-(S), 16-(R)-11
15-(S)-PPB-enol

The reduction may be carried out according to methods conventional in the art.

Reduction in the presence of silica gel with aqueous sodium borohydride (U.S. Pat. No. 6,482,959 B1) showed that the expected isomer was produced in larger amounts. After reduction, the isomer ratio in the crude product was PPB-enol:15-(S)-PPB-enol=6:4.

After the reduction, the quenched and worked-up reaction mixture was carried to the next reaction step, without separation of the diastereomers.

Step 5: Deprotection, Isolation and Crystallization

The last transformation is the removal of the p-phenylbenzoyl protecting group which can be carried out e.g. by the known method commonly used in prostaglandin chemistry, by methanolysis in the presence of potassium carbonate. Other reagents may also be used, e.g. NaOMe/methanol, NaOH or other base in a suitable aqueous-organic solvent mixture, or mineral acid in alcohol.

The desired product is then isolated from the resulting mixture. Isolation may be carried out using methods known in the art, such as crystallization or chromatography, or combinations thereof. Preferably, chromatography is applied, by which method the desired 15-epimer can be separated from the undesired epimer and from other impurities in one step.

Chromatography is preferably carried out for example on silica gel column with dichloromethane:acetone as eluent. The fractions containing the desired epimer are combined and evaporated.

The evaporation residue corresponds to hydroxyenol product of formula 1.

The hydroxyenol 1 can also be obtained in crystalline form, if desired, by crystallization of the residue from an ether type solvent or an ether type solvent mixture, preferably from a mixture of tert-butyl methyl ether and diisopropyl ether.

Yield: 48% hydroxyenol (1) in the form of an oil [calculated based on PPB-enone (16-(R)-10)]

Yield: 35% crystalline hydroxyenol (1) [calculated based on PPB-enone (16-(R)-10)]

Preparation of Racemic Phosphonate (3-(R,S)-4), Used as Starting Material

The racemic phosphonate (3-(R,S)-4) required for the HWE reaction can be prepared from known compounds by known chemical steps. For our experiments, the racemic phosphonate (3-(R,S)-4) was prepared in two ways, starting from 3-methylphenylacetic acid.

According to method A, methylphenylacetic acid (12) was alkylated in the first step, the resulting methylphenylpropionic acid (13) was converted to methyl ester (14), and the methyl ester was reacted with dimethyl methylphosphonate (DMMP) in the presence of a strong base, thereby obtaining racemic phosphonate (3-(R,S)-4).

According to method B, the first two steps were reversed, i.e. the starting methylphenylacetic acid (12) was first esterified with methanol, and the resulting methylphenylacetic acid methyl ester (15) was alkylated to obtain methylphenylpropionic acid methyl ester (14).

A).

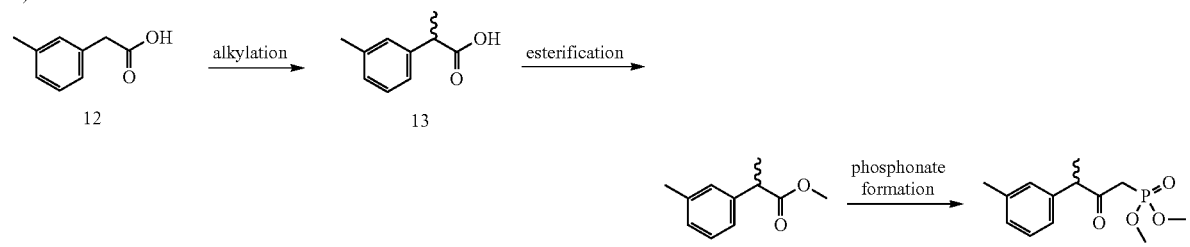

B.)

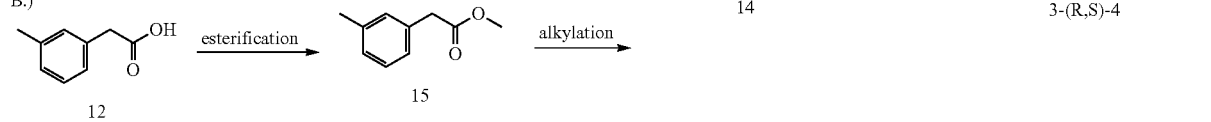

Method A)

Alkylation of methylphenylacetic acid (12) was carried out with methyl iodide, using butyl lithium or lithium diisopropylamide (LDA) as the base. Conversion was higher than 99.5% for both bases, but taking into account industrial feasibility, lithium diisopropylamide is preferred as it does not require deep freezing and it is safer to scale up.

Esterification of methylphenylpropionic acid (13) was performed with methanol in the presence of concentrated hydrochloric acid or concentrated sulphuric acid. Conversion was above 95% for both acids, so the use of the less corrosive sulphuric acid is considered more preferable.

The phosphonate (3-(R,S)-4) was prepared by reacting the methylphenylpropionic acid methyl ester (14) with dimethyl methylphosphonate (DMMP) in the presence of a strong base. The base used in this case, too, was butyl lithium or lithium diisopropylamide. The use of butyl lithium produced less by-products, but the reaction requires deep-freezing, while the reaction temperature for lithium diisopropylamide base is 0-10° C. (*J. Org. Chem.* 2009, 74, 7574-7576).

Method B)

In method B), methylphenylacetic acid (12) is esterified in the first reaction step. The esterification was carried out in methanol in the presence of concentrated sulphuric acid. The resulting methylphenylacetic acid methyl ester (15) was alkylated with methyl iodide in the presence of LDA.

The methylphenylpropionic acid methyl ester (14) thus obtained was converted to phosphonate (3-(R,S)-4) as described in method A).

The above methods (both A and B) provide an industrially applicable process for the preparation of 3-(R,S)-4.

The yield of the compound of formula 3-(R,S)-4 calculated based on methylphenylacetic acid (Route A, Example 8.1.2, 8.1.3 and 8.1.5) was 90.2%, (Route B, Example 8.2): 92.9%.

In summary, a novel process for the preparation of optically active hydroxyenol of formula 1 is disclosed. Hydroxyenol of formula 1 can be a valuable intermediate in the synthesis of prostaglandin and prostacyclin end products and derivatives, e.g. of those described in WO 2010029925 A1 and WO 2011111714 A1.

We have found that from readily available starting materials a new intermediate, 16-(R,S)-PPB-enone can be prepared, which is crystalline, and can be separated into diastereomers by fractional crystallization.

We have also found that the undesired isomer, 16-(S)-PPB-enone can be epimerized both in basic and acidic media. In the equilibrium reaction mixture, the ratio of diastereomers is PPB-enone:16-(S)-PPB-enone=1:1.

After the epimerization, fractional crystallization can provide additional amount of the desired isomer, PPB-enone.

PPB-enone and its 16-epimer, 16-(S)-PPB-enone, and 16-(R,S)-PPB-enone are novel compounds.

We have found that PPB-enone (16-(R)-10) can advantageously be reduced with an aqueous solution of sodium borohydride in the presence of silica gel. The ratio of diastereomers formed during the reduction is PPB-enol: 15-(S)-PPB-enol=6:4.

PPB-enol and its 15-epimer, 15-(S)-PPB-enol, and 15-(R, S)-PPB-enol are novel compounds.

Preferably, the compound of formula 16-(R,S)-10 can be prepared from optically active Corey lactone containing p-phenylbenzoyl (PPB) protecting group (8), which compound is available in prostaglandin chemistry in large quantities, and from racemic phosphonate of formula 3-(R,S)-4, which in turn can be prepared simply from inexpensive starting materials, by oxidation of the primary hydroxyl group of PPB-Corey lactone (8) and reacting the thus obtained PPB-Corey aldehyde (9) with the racemic phosphonate (3-(R,S)-4) in a Horner-Wadsworth-Emmons (HWE) reaction. The product, 16-(R,S)-PPB-enone, contains the diastereomers, which differ in the configuration of the 16-methyl group, in a ratio of 1:1.

In connection with the yields of the process of the invention and the known process, we note the followings:

Preparation of the phosphonate of formula 4 and racemic phosphonate of formula 3-(R,S)-4 (starting material used to form the side chain):

known process, chiral synthesis (Examples 1 and 2 of EP2343292):
yield of chiral phosphonate of formula 4 based on 2-(R)-(3-methylphenyl)propionic acid of formula 2: 75.9%
racemic synthesis described in this application:
route A) (examples 8.1.2, 8.1.3, and 8.1.5.): yield of racemic phosphonate of formula 3-(R,S)-4 based on racemic (3-methylphenyl)propionic acid of formula 13: 90.2%
route B) (example 8.2): yield of racemic phosphonate of formula 3-(R,S)-4 based on methylphenylacetic acid of formula 12: 92.9%

By the process described in this application the racemic phosphonate can be prepared from the racemic starting material in higher yields than the known chiral phosphonate from the corresponding chiral starting material (instead of 75.9%, the yield is 90.2% and 92.9% respectively; in the latter case, the yield is calculated from an earlier starting material).

Preparation of hydroxyenol of formula 1 from phosphonate of formula 4 and racemic phosphonate of formula 3-(R,S)-4, respectively:
  known process (Examples 3 to 5 of EP2343292):
  starting from chiral phosphonate of formula 4: 15.3%
  process according to the invention [Examples 1.b. (taking into account the yield based on 3-(R,S)-4), (2+5.4), 6, and 7, without crystallization]:
  starting from racemic phosphonate of formula (3-(R,S)-4): 14.8%
  relative to the good isomer, i.e. based on compound of formula 4: 29.6%

Starting from the racemic starting material we have almost reached the yield obtained starting from chiral starting material according to the known process, i.e. from a given amount of racemic starting material nearly the same amount of chiral target compound can be produced as from the same amount of chiral starting material by the known process. If we calculate for the "good" isomer, the yield is almost doubled from 15.3 to 29.6.

Preparation of hydroxyenol of formula 1 from chiral or racemic (3-methylphenyl)propionic acid (the above two stages together)
  known process (Examples 1 to 5 of EP2343292):
  based on 2-(R)-(3-methylphenyl)propionic acid (compound of formula 2): 11.6%
  process according to the invention [Examples 8.1.3., 8.1.5., 1.b (taking into account the yield based on 3-(R,S)-4), (2+5.4), 6, and 7, without crystallization]:
  based on 2-(R,S)-(3-methylphenyl)propionic acid (compound of formula 13): 13.3%
  relative to the good isomer, i.e. based on compound of formula 2: 26.6%

Starting from the racemic starting material we have exceeded the yield described for the chiral starting material. If calculated based on the "good" isomer, the yield is more than doubled from 11.6% to 26.6%.

Preparation of hydroxyenol of formula 1 from the "main" prostaglandin starting material:
  known process (Examples 3 to 5 of EP2343292):
  based on benzoyl-Corey aldehyde (5): 17.0%
  process according to the invention [Examples 1.b, (2+5.4), 6, and 7, without crystallization]: based on PPB-Corey lactone (8): 19.2%

A 2.2 percentage points increase was achieved in the yield, which corresponds to a relative increase of 13% (this value would be even higher if we could provide data for aldehyde, but the sensitive aldehyde was not isolated from the reaction mixture, so we take into account one more reaction step).

We note that since a racemic side chain is incorporated into the starting material, in principle, half of the material cannot form the desired end product. So if we did all the steps in the same way with the same efficiency, in theory, the yield would be half of that of the known process, namely 8.5% (compared to this we achieved 19.2%).

However, we have achieved, and even exceeded, the production of the known process, i.e., by incorporation of the racemic side chain and separation of the desired isomer at a later intermediate of the process (by fractional crystallization), we greatly increased the overall yield of the process. The increase in production is presumably due to several factors, including:

we avoid losses due to racemization of the chiral side chain, the separation of the racemic protected enon intermediate to its epimers by fractional crystallization is efficient (in addition, crystals containing a higher proportion of undesired isomers can be epimerized and further fractionated crystallization yields further desired isomers)

the reduction of the 15-oxo group is carried out more efficiently (and under milder reaction conditions).

In relation to the complete process starting from PPB-Corey lactone (8), we note the following:

It is more economical than the known processes because only one of the starting materials is optically active, the PPB-Corey lactone (8) which is available in large quantities. There is no need for costly resolution of the racemic phosphonate (3-(R,S)-4) or its costly stereoselective synthesis.

The total yield is higher than that of the known process.

The hydroxyenol (1) prepared according to our process is preferably crystallized, while in the known process the product is not crystallized; its appearance or state of matter is not described or characterized. However, a crystalline intermediate is easier to handle and generally more stable than other forms (e.g. oil).

The diastereomeric mixture containing p-phenylbenzoyl protecting group (16-(R,S)-PPB-enone) is crystalline, and the separation of the crystalline epimers of the diastereomeric enone became possible by fractional crystallization. It is noted that the difference between the 16-(R,S)-PPB-enone epimers is very little, only the small methyl group is in a different spatial position, so it is surprising that the epimers can be separated by fractional crystallization.

It has been found that the reduction of the 15-oxo group takes place under mild conditions, so that it is not necessary to use the method applying chiral reagent and $-40°$ C. described in WO 2010029925 A1 and WO 2011111714 A1.

The following non-limiting examples serve to illustrate the invention.

The X-ray, DSC and NMR recordings were taken using the following parameters:

X-Ray Diffractograms:
  Apparatus: Panalytical X'pert Pro
  Starting position [° 2Theta]: 2.0084
  End position [° 2Theta]: 39.9864
  Measurement temperature [° C.]: 25.00
  Anode material: Cu
  K-Alpha1 [Å]: 1.54060
  K-Alpha2 [Å]: 1.54443

DSC:
  Apparatus: METTLER TOLEDO DSC1 STARe System, Stare basic V9.30
  Method: Starting temperature: 30° C.
    End temperature: 150° C.
    Heating rate: 5° C./min
    Amount: 2-6 mg, perforated aluminum crucible (40 µl)

NMR:
  Apparatus: Bruker Avance III 500 MHz
  Solvent: DMSO

Example 1: Preparation of 16-(R,S)-PPB-enone

Oxidation and HWE reaction
[(3aR,4R,5R,6aS)-4-[(E)-4-(m-tolyl)-3-oxo-pent-1-enyl]-2-oxo-3,3a,4,5,6,6a-hexahydrocyclopenta[b]furan-5-yl] 4-phenylbenzoate

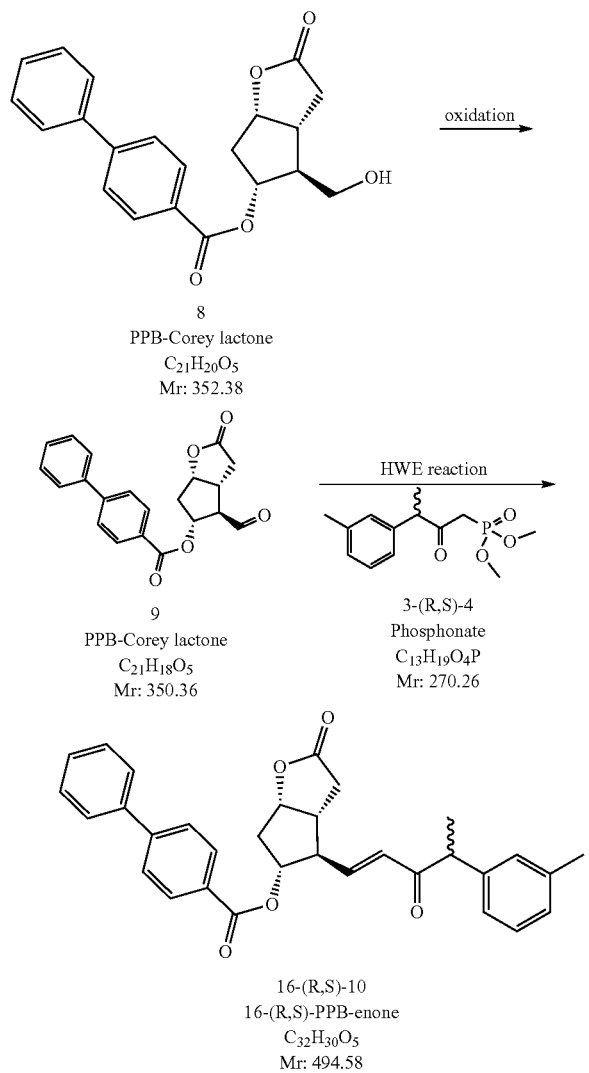

Example 1.a

Oxidation: Pfitzner-Moffatt Oxidation 5.94 kg of p-phenylbenzoyl-Corey lactone (PPB-Corey lactone) (8) was suspended in 41 kg of distilled toluene, 9.0 kg of N,N-dicyclohexylcarbodiimide was added, then, under an inert atmosphere, 3.4 L of a 0.75 M solution of phosphoric acid in dimethyl sulphoxide (DMSO) was added. After stirring for 30 minutes, the reaction mixture was heated to 50° C. The reaction mixture was stirred while maintaining the temperature, then 2×0.65 L of a 0.75 M phosphoric acid in DMSO was added every 30 minutes. After the addition of the second 0.65 L-portion of phosphoric acid in DMSO, it was stirred again for 30 min.

HWE Reaction

To the reaction mixture formed after the oxidation, containing the PPB-Corey aldehyde (9), the solution of the 3-(R,S)-4 phosphonate was added at −30° C. After the HWE reaction was complete (about 40 min), 67 L of a 1 M sodium hydrogen sulphate solution was added into the reaction mixture, and it was stirred for about 1.5 hours at room temperature. The crystalline reaction mixture was placed in a centrifuge and the centrifuged crystals were washed with 43 kg of dichloromethane. The filtrate and washing liquid were combined, washed neutral with 1 M sodium hydrogen carbonate solution, then with saturated sodium chloride solution, dried over sodium sulphate and evaporated. The evaporated concentrate was diluted with dichloromethane and then purified by chromatography on a silica gel column prepared with toluene, using a mixture of dichloromethane and ethyl acetate. The product-containing fractions were combined, concentrated at atmospheric pressure, and the concentrate was crystallized with isopropanol. The crystalline suspension was stirred at 0-5° C. to complete crystallization. The crystals were then filtered, washed, dried.

Yield: 5.56 kg (67%), m.p.: 127-146° C.

Preparation of the Phosphonate Solution (Base: Sodium Hydride):

To 15.6 kg of distilled toluene, 0.943 kg of sodium hydride were weighed in anhydrous atmosphere then, at 0° C., a solution of 6.15 kg of 3-(R,S)-4 phosphonate in 11 L of distilled toluene was added at 0-10° C. After the addition, the cooling was stopped and the reaction mixture was stirred until complete dissolution.

Example 1.b

Oxidation: Anelli Oxidation

To a mixture of 640 mL of dichloromethane and 33.5 mL of isopropanol 2.6 g of potassium bromide, 55.1 g of sodium hydrogen carbonate, 77.0 g of PPB-Corey lactone (8), 0.683 g of TEMPO and 540 mL of dichloromethane were added. With vigorous stirring, the reaction mixture was cooled to −5 to 0° C. and 119 mL of sodium hypochlorite solution (1.93 M aqueous solution) was added, then stirred while maintaining the temperature. When the oxidation is complete, 390 mL of water and 77 mL of 20% sodium thiosulfate solution were added to the reaction mixture at 10-20° C. After the addition, the reaction mixture was stirred at 30-35° C. for about 30 minutes, and then the phases were separated, and the aqueous phase was extracted with 130 mL of dichloromethane. The combined organic phase contained the 9 PPB-Corey aldehyde, which was used in the next reaction step (HWE reaction) without further purification.

HWE Reaction

To the solution of the phosphonate cooled to 0-5° C., the solution of PPB-Corey aldehyde (9) formed in the oxidation step was added under an inert atmosphere, and then the reaction mixture was stirred while maintaining the temperature. After completion of the reaction, the reaction mixture was poured onto 180 ml of a 2 M sodium hydrogen sulphate solution at 5-10° C., and after stirring, the phases were separated, the organic phase was concentrated under reduced pressure and the solvent of the concentrate was changed to isopropanol. During the concentration, crystallization begins. Additional isopropanol was added to the crystalline reaction mixture, which was then stirred at 0-5° C. for 3 hours. The crystals were filtered, washed with chilled isopropanol and dried.

Yield: 91.86 g (85%).

Preparation of the Phosphonate Solution (Base: Aqueous Solution of Potassium Hydroxide):

76.77 g of phosphonate (3-(R,S)-4) was weighed at room temperature, under inert atmosphere, into 146 mL of dichloromethane, and a solution of 14.68 g of potassium hydroxide in 24.6 mL of water was added. After complete dissolution, the reaction mixture was cooled to 0° C.

The DSC curve of 16-(R,S)-PPB-enone is shown in FIG. 1.

Figure 2:
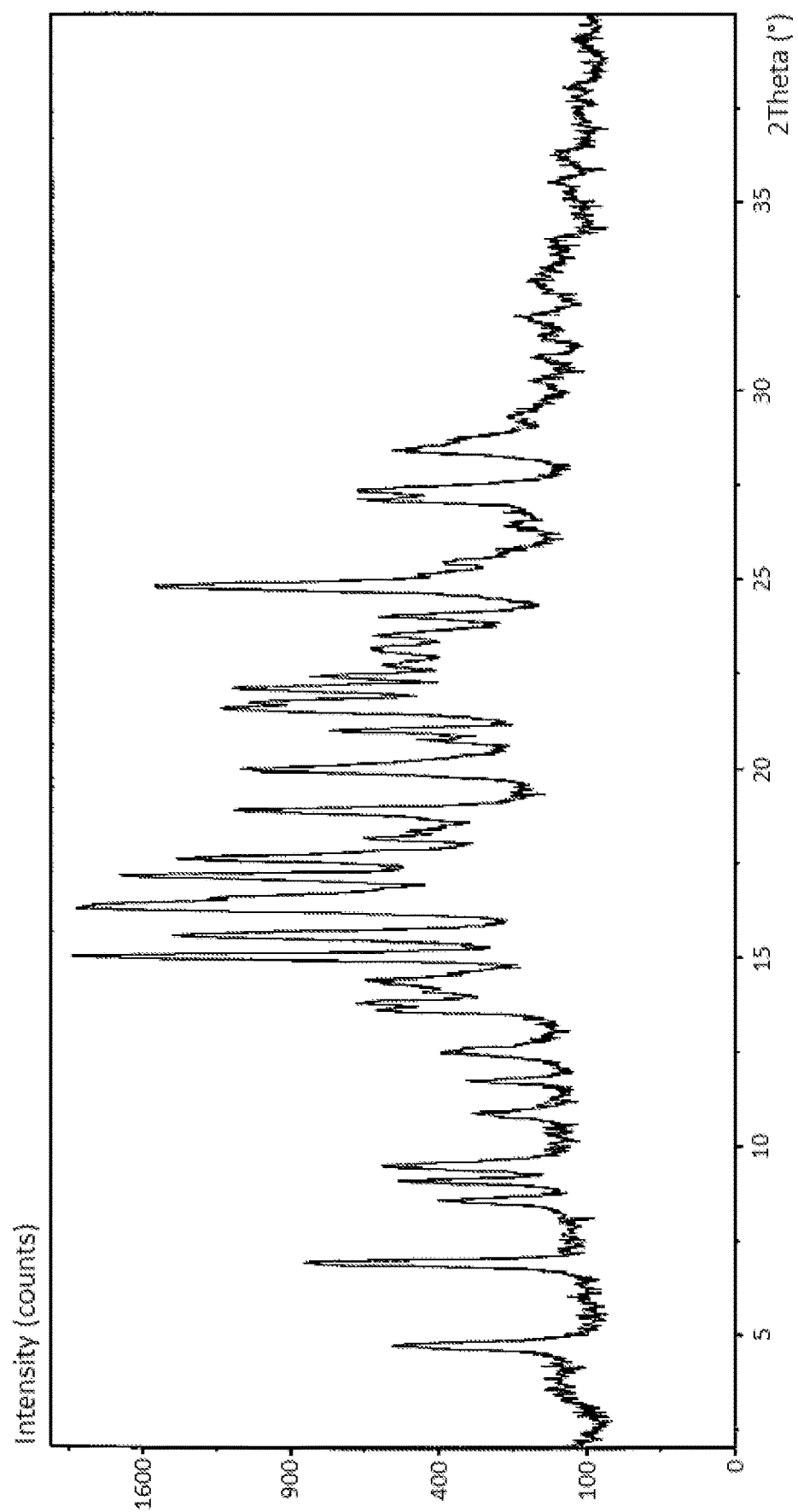
FIG. 2 shows a powder X-ray diffraction pattern of 16-(R,S)-PPB-enone prepared according to Example 1.

The powder X-ray diffraction pattern of 16-(R,S)-PPB-enone is shown in FIG. 2, the characteristic peaks are listed in Table 1 below.

TABLE 1

| Pos. [° 2Th.] | Height [cts] | FWHM [° 2Th.] | d-spacing [A] | Rel. Int. [%] |
|---|---|---|---|---|
| 4.7281 | 411.58 | 0.1673 | 18.69011 | 23.32 |
| 6.9238 | 720.36 | 0.1338 | 12.76713 | 40.81 |
| 8.561 | 251.08 | 0.1338 | 10.32887 | 14.23 |
| 9.0748 | 375.65 | 0.1338 | 9.74511 | 21.28 |
| 9.4847 | 417.66 | 0.1673 | 9.32493 | 23.66 |
| 11.7331 | 176.16 | 0.1338 | 7.54252 | 9.98 |
| 12.519 | 231.48 | 0.2007 | 7.07074 | 13.12 |
| 13.7283 | 324.56 | 0.3346 | 6.45051 | 18.39 |
| 14.3662 | 375.96 | 0.1673 | 6.16548 | 21.30 |
| 15.0253 | 1764.96 | 0.1840 | 5.89648 | 100.00 |
| 15.5773 | 1180.91 | 0.1840 | 5.68877 | 66.91 |
| 16.3161 | 1685.63 | 0.1338 | 5.43278 | 95.51 |
| 17.1626 | 1374.56 | 0.1506 | 5.16669 | 77.88 |
| 17.6125 | 1033.93 | 0.1338 | 5.03571 | 58.58 |
| 18.8958 | 828.56 | 0.1506 | 4.69651 | 46.94 |
| 19.9821 | 790.15 | 0.1506 | 4.44358 | 44.77 |
| 20.9746 | 455.34 | 0.1004 | 4.2355 | 25.80 |
| 21.5481 | 835.01 | 0.1338 | 4.12406 | 47.31 |
| 22.1082 | 676.73 | 0.1338 | 4.02082 | 38.34 |
| 23.5058 | 182.44 | 0.2007 | 3.78482 | 10.34 |
| 24.0174 | 286.38 | 0.1673 | 3.70535 | 16.23 |
| 24.7971 | 1279.74 | 0.1840 | 3.59058 | 72.51 |

TABLE 1-continued

| Pos. [° 2Th.] | Height [cts] | FWHM [° 2Th.] | d-spacing [A] | Rel. Int. [%] |
|---|---|---|---|---|
| 27.3471 | 434.99 | 0.1338 | 3.26129 | 24.65 |
| 28.4247 | 320.13 | 0.1673 | 3.14006 | 18.14 |

Assignment of the $^{13}$C and $^1$H NMR spectra of 16-(R,S)-PPB-enone are shown in Table 2 below.

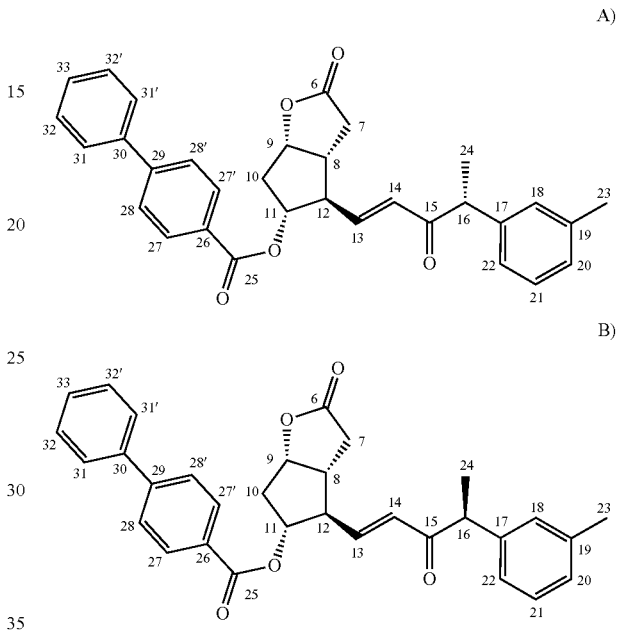

Structure and numbering of PPB-enone (A) and 16-(S)-PPB-enone (B) as used for NMR data

TABLE 2

| Numbering | $^{13}$C (ppm) | $^1$H (ppm) | Number of $^1$H | Multiplicity | Coupling constant (Hz) (+/− 0.2 Hz) |
|---|---|---|---|---|---|
| 6 | 176.39 | — | — | | |
| 7 | 34.15 | β: 2.88* | 1 | m | |
| | | α: 2.40**, 2.42** | 1 | m | |
| 8 | 41.99 | 2.87* | 1 | m | |
| 9 | 82.98$; 82.93$ | 5.055*** | 1 | m (td) | $J_{8,9}$~6.0; $J_{9,10\alpha}$~1.5 |
| 10 | 37.34 | β: 2.555⁺; 2.57⁺ | 1 | m (dt) | $J_{gem}$ = 15.0/15.1; $J_{9,10\beta}$ = $J_{10\beta,11}$ = 6.6 |
| | | α: 2.05⁺⁺ | 1 | m | |
| 11 | 78.70$; 78.63$ | 5.215 | 1 | m (td/q) | $J_{11,12}$ = 5.5 |
| 12 | 53.12$; 53.16$ | 2.94* | 1 | m | |
| 13 | 144.74; 144.56 | 6.82⁺⁺⁺; 6.81⁺⁺⁺ | 1 | m (dd) | $J_{13,14}$ = 15.7; $J_{12,13}$ = 8.1/8.2 |
| 14 | 129.53$; 129.56$ | 6.27&; 6.28& | 1 | m (d) | |
| 15 | 198.99; 198.90 | — | — | | |
| 16 | 49.28; 49.51 | 4.10&&; 4.09&& | 1 | m (q) | $J_{16,24}$ = 6.6 |
| 17 | 140.43$; 140.38$ | — | — | | |

TABLE 2-continued

| Numbering | $^{13}C$ (ppm) | $^1H$ (ppm) | Number of $^1H$ | Multiplicity | Coupling constant (Hz) (+/− 0.2 Hz) |
|---|---|---|---|---|---|
| 18 | 128.34$ | 7.00&&& | 1 | m (s) | |
| 19 | 137.72$; 137.71$ | — | — | — | |
| 20 | 127.41 | 6.97&&& | 1 | m (d) | |
| 21 | 128.48$; 128.47$ | 7.14#; 7.125# | 1 | m (t) | $J_{20,21} = J_{21,22} = 7.3$ |
| 22 | 124.86$; 124.90$ | 6995&&& | 1 | m (d) | |
| 23 | 20.88 | 2.215##; 2.20** | 3 | m (s) | |
| 24 | 17.30$; 17.36$ | 1.275### | 3 | d | |
| 25 | 164.81 | — | — | — | |
| 26 | 128.08 | — | — | — | |
| 27, 27' | 129.83$; 129.81$ | 7.95¹; 7.93¹ | 2 | m (d) | $J_{26,27} = 8.3$ |
| 28, 28' | 126.77 | 7.795ᴴ, 7.78ᴴ | 2 | m (d) | |
| 29 | 144.83$, 144.82$ | — | — | — | |
| 30 | 138.75 | — | — | — | |
| 31, 31' | 126.94 | 7.74ᴴ | 2 | m (d) | |
| 32, 32' | 129.05$; 129.06$ | 7.51ᴵᴵᴵ; 7.505ᴵᴵᴵ | 2 | m (t) | $J_{31,32} = 7.5$ |
| 33 | 128.38$ | 7.43ᴸ, 7.435ᴸ | 1 | m (t) | $J_{32,33} = 7.4$ |

$Partly overlapped by the $^{13}C$ NMR signals.
$$Partly overlapped $^{13}C$ NMR signals.
*, **, †, ††, †††, &, &&, &&&, #, ##, ¹, ᴵᴵ, ᴵᴵᴵ, ᴸ Partly overlapped $^1H$ NMR signals.
†Partly overlapped by the $^1H$ NMR signal of the DMSO-$d_6$ solvent.
***, ††, &, &&&, ##, ### Partly overlapped by the $^1H$ NMR signals of the sample unknown impurities.

Example 2 (Reference Example): Preparation of PPB-Enone (16-(R)-10)

Column Chromatography

[(3aR,4R,5R,6aS)-4-[(E,4R)-4-(m-tolyl)-3-oxo-pent-1-enyl]-2-oxo-3,3a,4,5,6,6a-hexahydrocyclopenta[b]furan-5-yl] 4-phenylbenzoate

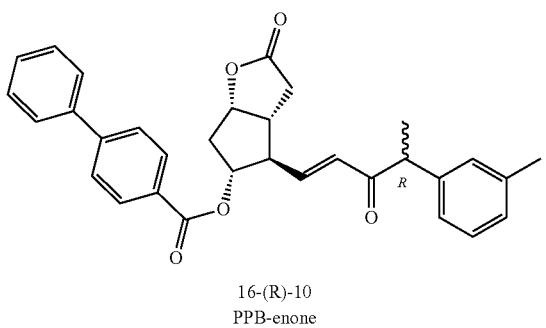

16-(R,S)-10
16-(R,S)-PPB-enone
$C_{32}H_{30}O_5$
Mr: 494.58

1.595 g of 16-(R,S)-PPB-enone (16-(R,S)-10) was dissolved in 5 ml of chloroform:tert-butyl methyl ether=30:1. Chromatography was carried out on a column made of 50 g of silica gel, using chloroform:tert-butyl methyl ether=30:1 and 10:1 as eluent.

First the epimer of formula 16-(R)-10, and thereafter the epimer of formula 16-(S)-10 were eluted, both as oil.

Yield: PPB-enone: 0.367 g, 23% (oil which crystallizes on standing)

16-(S)-PPB-enon: 0.073 g, 4.6% (oil which crystallizes on standing)

The obtained crystals can be used as seed crystals in the fractional crystallization.

Example 3: Preparation of PPB-Enone (16-(R)-10)

Fractional Crystallization

[(3aR,4R,5R,6aS)-4-[(E,4R)-4-(m-tolyl)-3-oxo-pent-1-enyl]-2-oxo-3,3a,4,5,6,6a-hexahydrocyclopenta[b]furan-5-yl] 4-phenylbenzoate

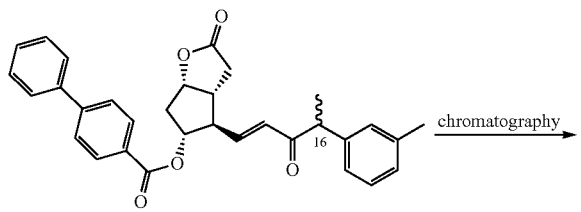

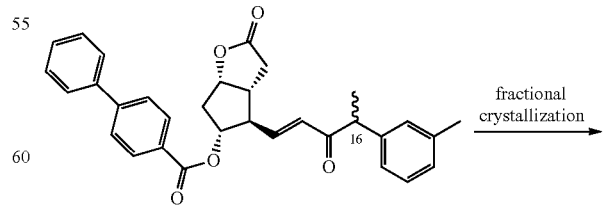

16-(R)-10
PPB-enone
$C_{32}H_{30}O_5$
Mr: 494.58

16-(R,S)-10
16-(R,S)-PPB-enone
$C_{32}H_{30}O_5$
Mr: 494.58

-continued

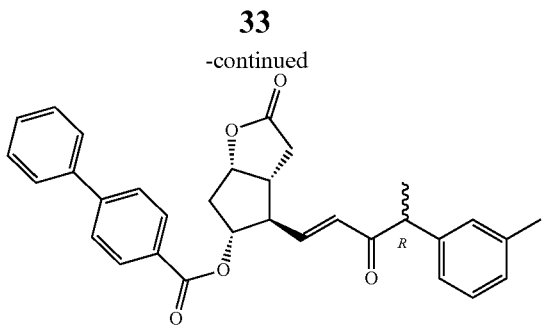

16-(R)-10
PPB-enone
C$_{32}$H$_{30}$O$_5$
Mr: 494.58

Example 3.a.: Fractional Crystallization with tert-butyl methyl ether 5.58 kg of 16-(R,S)-PPB-enone (16-(R,S)-10) were suspended in 167 L of tert-butyl methyl ether and then heated to reflux. After refluxing for about 30 minutes, the mixture was cooled to 30-32° C. and stirred for a further 30 minutes, while maintaining the temperature. The crystals (K$_{r1}$) were filtered, washed, dried. First, the undesired isomer, 16-(S)-PPB-enone, was precipitated; in the crystals filtered, the ratio of 16-(S)-PPB-enone:PPB-enone was about 78:22.

The filtrate combined with the washing liquid was seeded with PPB-enone crystals (16-(R)-10), the suspension was cooled to 0-5° C. and stirred for 1 hour, while maintaining the temperature. The crystals (K$_{r2}$, PPB-enone, 16-(R)-10) were filtered, washed with cold tert-butyl methyl ether and dried.

In the filtrate combined with the washing liquid, the previously filtered K$_{r1}$ crystals (16-(S)-PPB-enone, 16-(S)-10) were suspended, and the suspension was heated to reflux. After refluxing for about 30 minutes, the mixture was cooled to 30-32° C. and stirred for 1 additional hour, while maintaining the temperature. The crystals (K$_{r3}$, 16-(S)-PPB-enone, 16-(S)-10) were filtered, washed, dried.

Yield of 16-(S)-PPB-enone: 2.706 kg (48.5%), purity greater than 85% (HPLC)

The 16-(S)-PPB-enone can be further purified according to Example 4.

The filtrate combined with the washing liquid was seeded with PPB-enone (16-(R)-10), cooled to 0-5° C., and was stirred for 1 hour, while maintaining the temperature. The crystals (K$_{r4}$) (PPB-enone, 16-(R)-10) were filtered, washed with cold (0-5° C.) tert-butyl methyl ether and dried.

Yield of PPB-enone (K$_{r2}$ and K$_{r4}$ crystals): 1.71 kg (31%) colorless crystals.

The combined PPB-enone (16-(R)-10) crystals were dissolved in tert-butyl methyl ether:dichloromethane=5:1 mixture (10.3 L) at 40-42° C., and about 25 L of tert-butyl methyl ether was added thereto, seeded with PPB-enone (16-(R)-10), after stirring for about 30 minutes, the suspension was cooled to 0-5° C. After stirring for about 1 hour, the crystals were filtered, washed with cold tert-butyl methyl ether and dried.

Yield: 1.67 kg (98%), colourless crystal.

Yield of PPB-enone obtained by fractional crystallization (in TBME solvent) of the diastereomeric mixture 16-(R,S)-PPB-enone: 1.67 kg (30%).

The isomer ratio in the thus obtained PPB-enone product, determined by HPLC:

PPB-enone:16-(S)-PPB-enone=99.6:0.4

Figure 3:
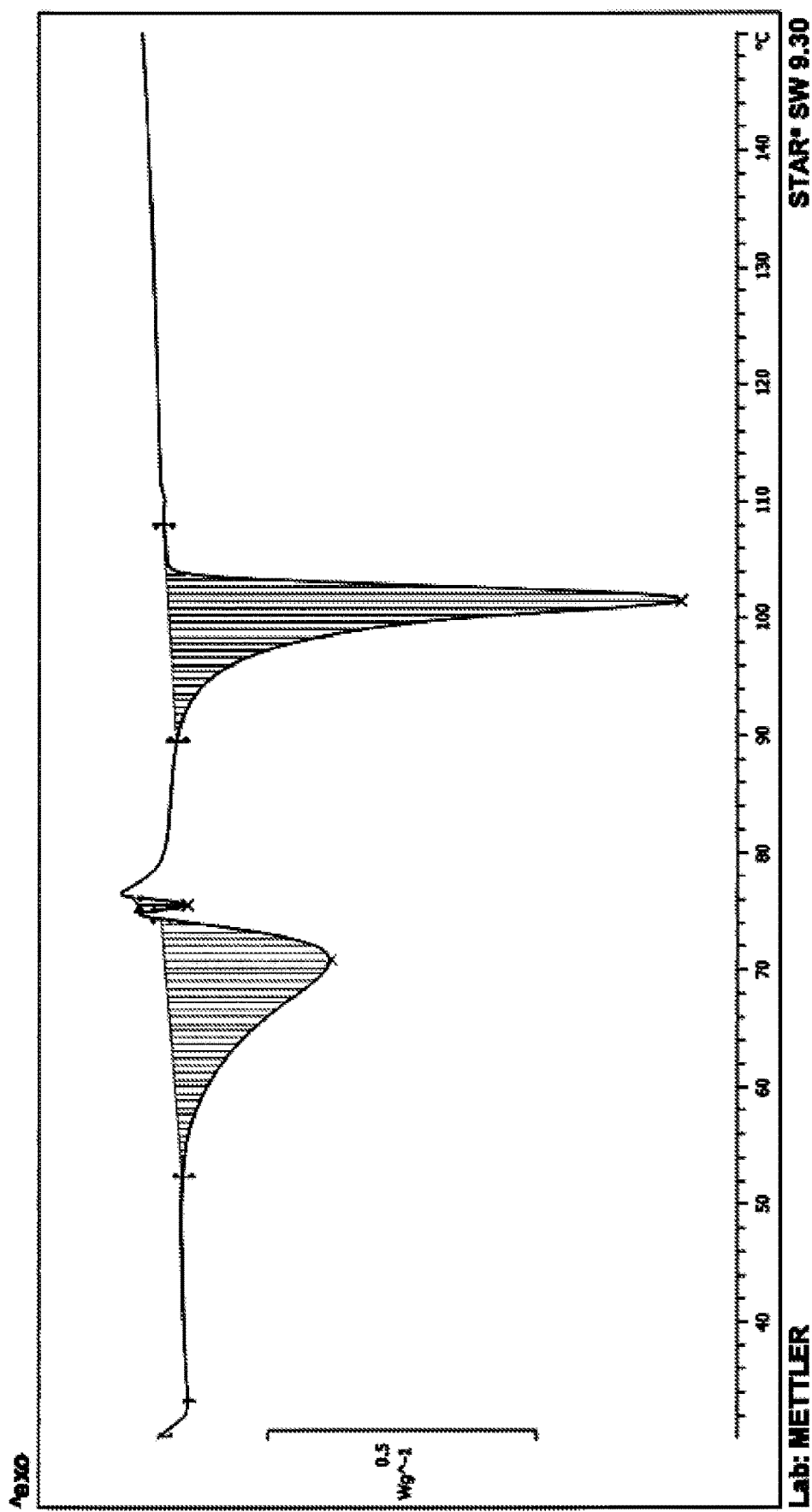

The DSC curve of PPB-enone is shown in FIG. 3.

Figure 4:
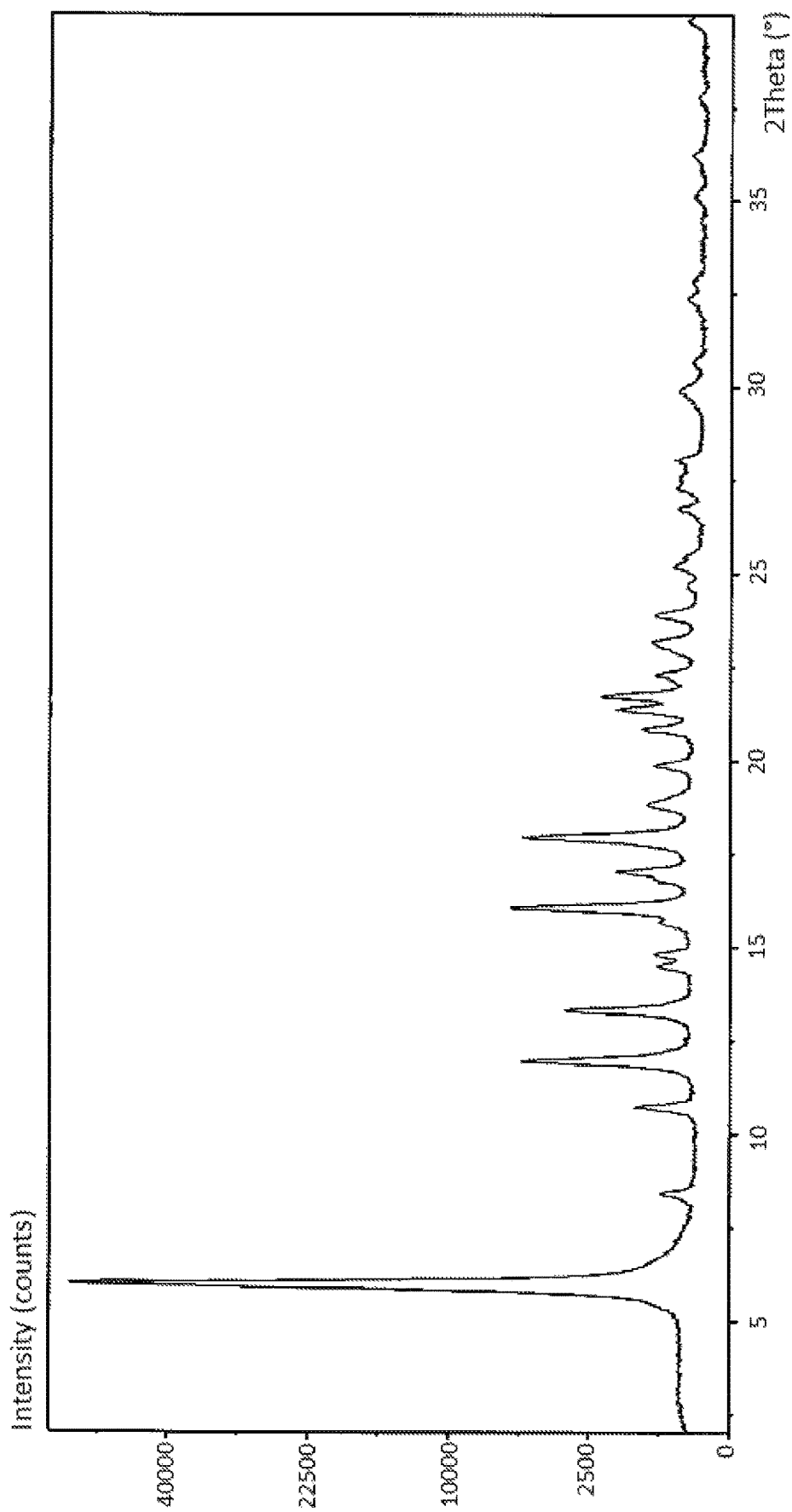

The powder X-ray diffraction pattern of PPB-enone is shown in FIG. 4, the characteristic peaks are listed in Table 3 below.

TABLE 3

| Pos. [° 2Th.] | Height [cts] | FWHM [° 2Th.] | d-spacing [A] | Rel. Int. [%] |
| --- | --- | --- | --- | --- |
| 5.9976 | 54895.50 | 0.1506 | 14.73644 | 100.00 |
| 8.3949 | 428.96 | 0.1338 | 10.53281 | 0.78 |
| 10.7180 | 986.68 | 0.1171 | 8.2545 | 1.80 |
| 11.9390 | 5359.41 | 0.1506 | 7.4129 | 9.76 |
| 13.3092 | 3242.96 | 0.1506 | 6.6527 | 5.91 |
| 14.4881 | 503.25 | 0.1506 | 6.11389 | 0.92 |
| 14.7925 | 562.21 | 0.1673 | 5.98875 | 1.02 |
| 15.6526 | 479.70 | 0.1338 | 5.66158 | 0.87 |
| 16.0353 | 5853.37 | 0.1506 | 5.52728 | 10.66 |
| 17.0078 | 1525.66 | 0.1338 | 5.21337 | 2.78 |
| 17.9168 | 5296.31 | 0.1673 | 4.95087 | 9.65 |
| 18.8006 | 737.65 | 0.2007 | 4.72008 | 1.34 |
| 19.8465 | 586.90 | 0.1004 | 4.47365 | 1.07 |
| 20.8062 | 903.63 | 0.1506 | 4.2694 | 1.65 |
| 21.3792 | 1530.44 | 0.1673 | 4.15626 | 2.79 |
| 21.7313 | 1999.10 | 0.1338 | 4.08971 | 3.64 |
| 22.3061 | 600.10 | 0.1171 | 3.9856 | 1.09 |
| 23.1873 | 669.17 | 0.1338 | 3.8361 | 1.22 |
| 23.9038 | 612.76 | 0.1338 | 3.7227 | 1.12 |
| 24.6774 | 124.15 | 0.2007 | 3.60773 | 0.23 |
| 25.2215 | 277.78 | 0.1673 | 3.53112 | 0.51 |
| 26.7521 | 233.75 | 0.2007 | 3.33247 | 0.43 |
| 27.3158 | 255.78 | 0.1338 | 3.26497 | 0.47 |
| 28.0327 | 249.46 | 0.1673 | 3.18307 | 0.45 |
| 29.9100 | 243.52 | 0.2007 | 2.98743 | 0.44 |
| 30.6669 | 84.71 | 0.2007 | 2.9154 | 0.15 |
| 32.3799 | 135.70 | 0.2007 | 2.76497 | 0.25 |
| 35.1114 | 74.33 | 0.2676 | 2.55588 | 0.14 |
| 36.1886 | 98.73 | 0.2676 | 2.48224 | 0.18 |
| 37.7207 | 43.33 | 0.4015 | 2.38486 | 0.08 |

Assignment of the $^{13}$C and $^1$H NMR spectra of PPB-enone is given in table 4 below.

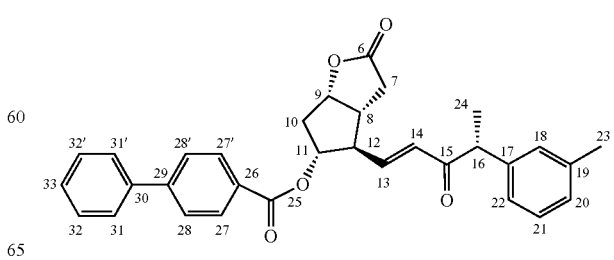

Structure and Numbering of PPB-Enone as Used for NMR Data

TABLE 4

| Numbering | $^{13}$C (ppm) | $^1$H (ppm) | Number of $^1$H | Multiplicity | Coupling constant (Hz) (+/− 0.2 Hz) |
|---|---|---|---|---|---|
| 6 | 176.42 | — | — | | |
| 7 | 34.15 | β: 2.87* | 1 | m | |
|   |  | α: 2.40 | 1 | m | |
| 8 | 41.99 | 2.87* | 1 | m | |
| 9 | 83.00 | 5.055 | 1 | m (t/td) | $J_{8,9} \sim J_{9,10\beta} \sim 6.4$, $J_{9,10\alpha} \sim 1.5$ |
| 10 | 37.34 | β: 2.55$^\&$ | 1 | m (dt) | $J_{gem} \sim 15.1$, |
|   |  | α: 2.05 | 1 | m (dd) | $J_{10\beta,11} = 6.4$ $J_{10\alpha,11} \sim 4.6$ |
| 11 | 78.71 | 5.21 | 1 | m (td/q) | $J_{11,12} = 5.4$ |
| 12 | 53.13 | 2.95 | 1 | m (dt/ddd) | |
| 13 | 144.78$ | 6.815 | 1 | dd | $J_{13,14} = 15.7$; $J_{12,13} = 8.2$ |
| 14 | 129.54 | 6.27 | 1 | d | |
| 15 | 199.01 | — | — | | |
| 16 | 49.27 | 4.10 | 1 | q | $J_{16,24} = 6.8$ |
| 17 | 140.44 | — | — | | |
| 18 | 128.35$ | 7.01*** | 1 | m (s) | |
| 19 | 137.74 | — | — | | |
| 20 | 127.44 | 6.97*** | 1 | m (d) | |
| 21 | 128.50 | 7.14 | 1 | m (t) | $J_{20,21} = J_{21,22} = 7.5$ |
| 22 | 124.88 | 7.00*** | 1 | m (d) | |
| 23 | 20.90 | 2.22 | 3 | m (s) | |
| 24 | 17.32 | 1.275 | 3 | d | |
| 25 | 164.82 | — | — | | |
| 26 | 128.09 | — | — | | |
| 27, 27' | 129.84 | 7.94$^\#$ | 2 | m (d) | $J_{26,27} = 8.2$ |
| 28, 28' | 126.79 | 7.80$^{\#\#}$ | 2 | m (d) | |
| 29 | 144.84$ | — | — | | |
| 30 | 138.75 | — | — | | |
| 31, 31' | 126.96 | 7.74$^{\#\#}$ | 2 | m (d) | $J_{31,32} = 7.5$ |
| 32, 32' | 129.06 | 7.51 | 2 | m (t) | |
| 33 | 128.41$ | 7.43 | 1 | m (t) | $J_{32,33} = 7.3$ |

$Partly overlapped $^{13}$C NMR signals.
*, , *, $^{\#\#}$Partly overlapped $^1$H NMR signals.
$^\#$Partly overlapped by the $^1$H NMR signals of the sample impurity.
$^\&$Overlapped $^1$H NMR signal of the DMSO solvent.

Example 3.b: Fractional Crystallization with Methanol 5.58 g of 16-(R,S)-PPB-enone (16-(R,S)-10) was suspended in 167 mL of methanol and then heated to reflux. After refluxing for about 30 minutes, the mixture was cooled to 30-32° C. and stirred for a further 30 minutes, while maintaining the temperature. The crystals (K$_{r1}$) were filtered, washed, dried. First, the undesired isomer, 16-(S)-PPB-enone, was precipitated.

The filtrate combined with the washing liquid was seeded with PPB-enone crystals (16-(R)-10), the suspension was cooled to 0-5° C. and stirred for 1 hour. The crystals (K$_{r2}$, PPB-enone, 16-(R)-10) were filtered, washed with cold (0-5° C.) methanol and dried.

In the filtrate combined with the washing liquid, the previously filtered K$_{r1}$ crystals (16-(S)-PPB-enone, 16-(S)-10) were suspended, and the suspension was heated to reflux. After refluxing for about 30 minutes, the mixture was cooled to 30-32° C. and stirred for 1 additional hour, while maintaining the temperature. The crystals (K$_{r3}$, 16-(S)-PPB-enone, 16-(S)-10) were filtered, washed, dried. This gave 2.9 g of K$_{r3}$ crystals (yield 52%), purity greater than 78% (HPLC).

The filtrate combined with the washing liquid was seeded with PPB-enone (16-(R)-10), cooled to 0-5° C., and was stirred for 1 hour, while maintaining the temperature. The crystals (K$_{r4}$) (PPB-enone, 16-(R)-10) were filtered, washed with cold methanol and dried.

Yield (K$_{r2}$ and K$_{r4}$ crystals): 1.69 kg (30%) colorless crystals.

The combined PPB-enone (16-(R)-10) crystals were dissolved in methanol:dichloromethane=5:1 mixture at 40-42° C., and about 25 mL of methanol was added thereto, seeded with PPB-enone (16-(R)-10), and after stirring for about 30 minutes, the suspension was cooled to 0-5° C. After stirring for about 1 hour, the crystals were filtered, washed with cold methanol and dried.

The precipitated crystals were dissolved in methanol:dichloromethane=5:1 and the above crystallization was repeated.

Yield (for the two recrystallization steps): 1.62 g (96%), colourless crystal.

Yield of PPB-enone obtained by fractional crystallization (in methanol solvent) of the diastereomeric mixture 16-(R,S)-PPB-enone: 1.62 g (29%).

The isomer ratio in the thus obtained PPB-enone product, determined by HPLC:

PPB-enone:16-(S)-PPB-enone=97.89:2.11

Note: When repeating the process several times, at about every fourth repeat, the amount of K$_{r2}$+K$_{r4}$ crystals precipitated increased from 1.69 g to 1.70-1.75 g, and contained more than 10% of the undesired epimer, 16-(S)-PPB-enone.

Figure 5:
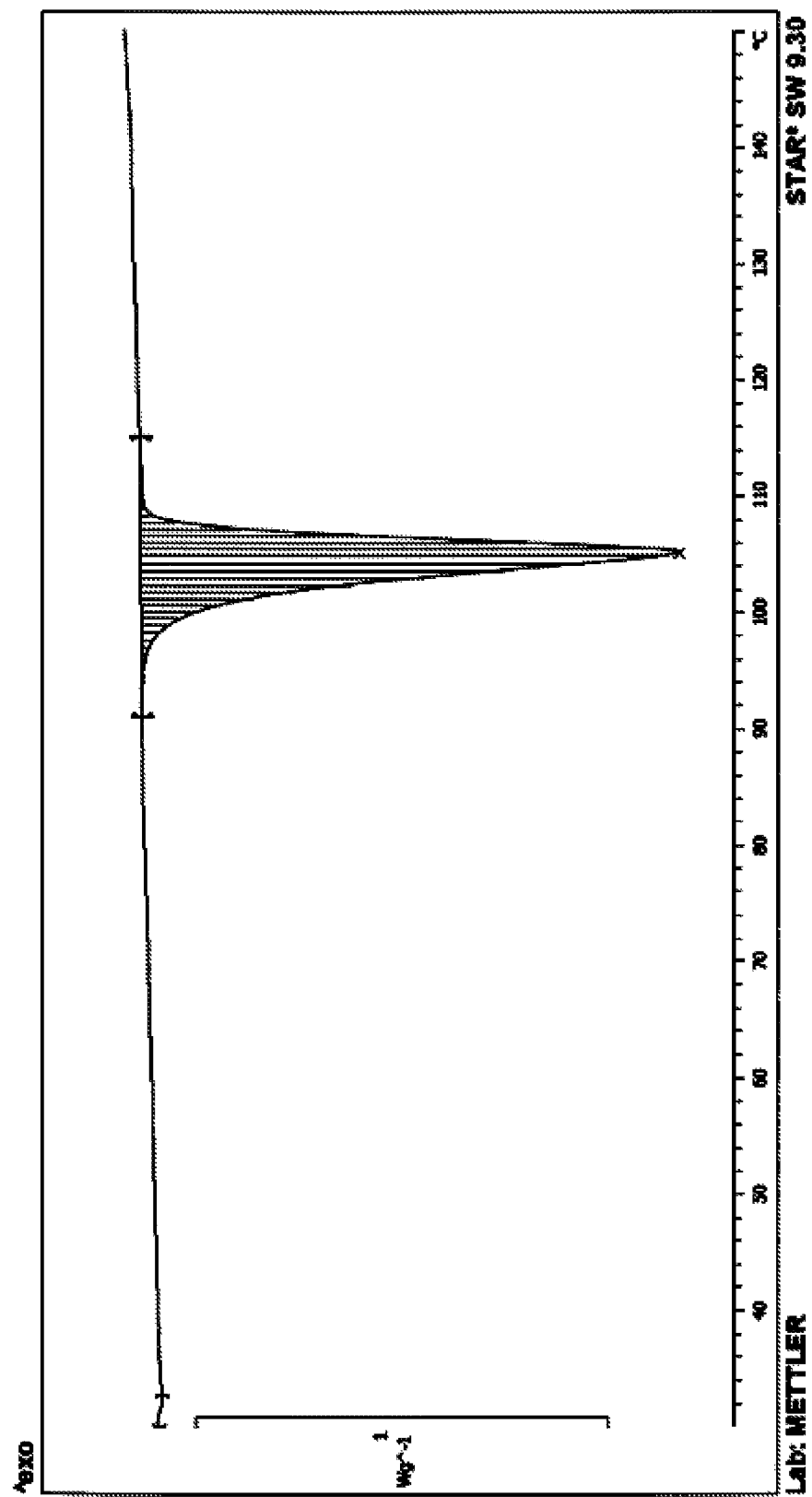
FIG. 5 shows a DSC curve of 16-(R)-PPB-enone prepared according to Example 3.b.

The DSC curve of PPB-enone is shown in FIG. 5.

Figure 6:
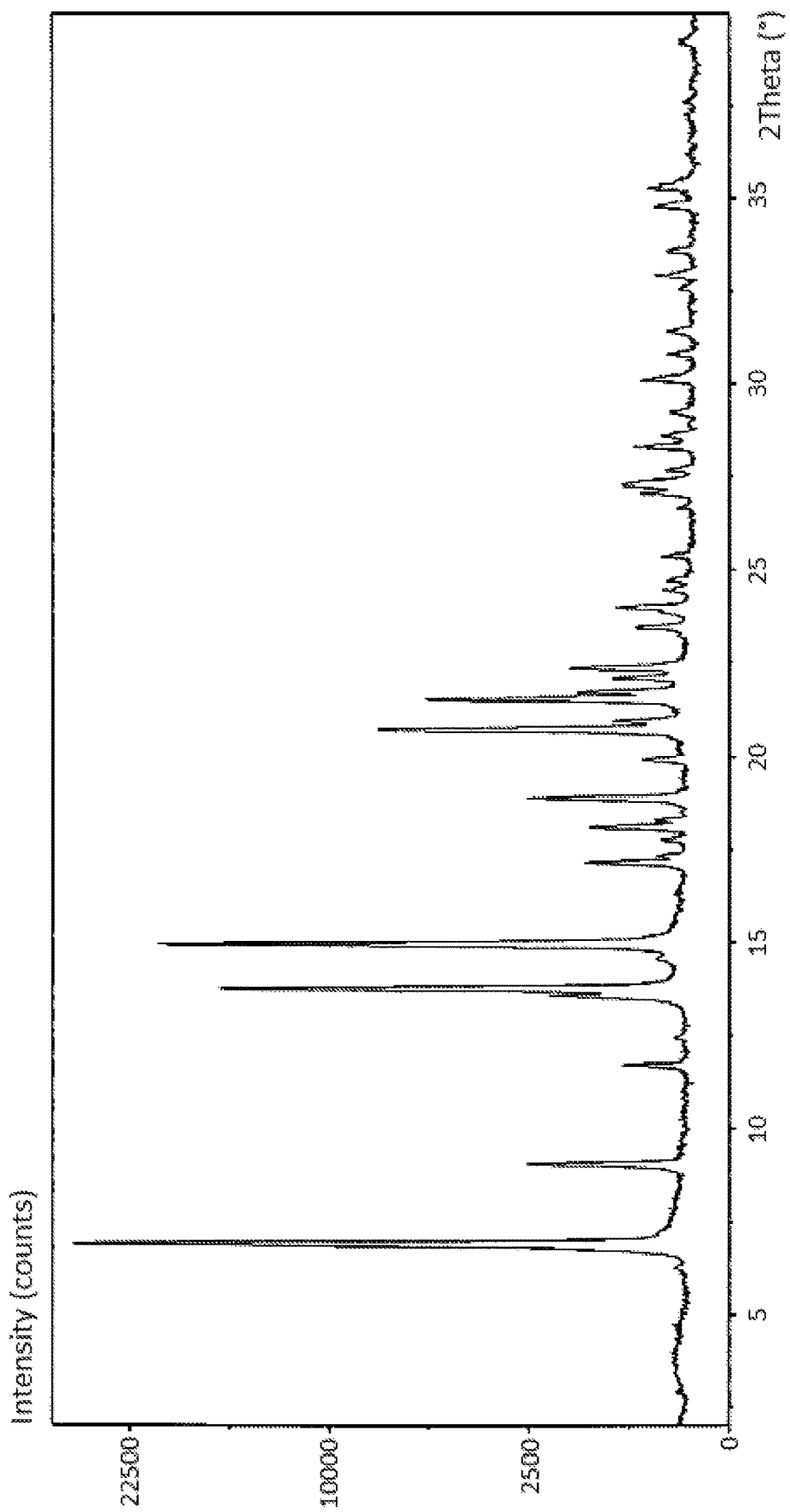
FIG. 6 shows a powder X-ray diffraction pattern of 16-(R)-PPB-enone prepared according to Example 3.b.

The powder X-ray diffraction pattern of PPB-enone is shown in FIG. 6, the characteristic peaks are listed in Table 5 below.

TABLE 5

| Pos.<br>[° 2Th.] | Height<br>[cts] | FWHM<br>[° 2Th.] | d-spacing<br>[A] | Rel. Int.<br>[%] |
|---|---|---|---|---|
| 6.8973 | 27142.83 | 0.0836 | 12.81612 | 100.00 |
| 9.0322 | 2414.84 | 0.0836 | 9.79098 | 8.90 |
| 11.6877 | 582.13 | 0.0836 | 7.57172 | 2.14 |
| 13.5649 | 1859.21 | 0.0669 | 6.52785 | 6.85 |
| 13.7652 | 16087.77 | 0.0836 | 6.4333 | 59.27 |
| 14.9575 | 20031.13 | 0.1004 | 5.92306 | 73.80 |
| 17.1285 | 1177.98 | 0.0836 | 5.1769 | 4.34 |
| 18.0751 | 1091.85 | 0.1004 | 4.90787 | 4.02 |
| 18.8519 | 2397.06 | 0.1004 | 4.70736 | 8.83 |
| 19.9188 | 343.93 | 0.0836 | 4.45757 | 1.27 |
| 20.6806 | 7288.55 | 0.1004 | 4.29505 | 26.85 |
| 20.9086 | 730.48 | 0.0836 | 4.24874 | 2.69 |
| 21.5010 | 5634.87 | 0.1004 | 4.13298 | 20.76 |
| 21.7022 | 1312.53 | 0.0836 | 4.09513 | 4.84 |
| 22.0699 | 717.58 | 0.0836 | 4.02772 | 2.64 |
| 22.3485 | 1467.09 | 0.1171 | 3.97814 | 5.41 |
| 23.4430 | 426.40 | 0.1004 | 3.79482 | 1.57 |
| 23.9803 | 653.61 | 0.1171 | 3.71101 | 2.41 |
| 24.4513 | 134.78 | 0.1338 | 3.64058 | 0.50 |
| 27.0355 | 373.97 | 0.0669 | 3.29818 | 1.38 |
| 27.2880 | 589.86 | 0.1673 | 3.26823 | 2.17 |
| 28.2939 | 460.20 | 0.0669 | 3.15429 | 1.70 |
| 29.2302 | 109.09 | 0.1338 | 3.05534 | 0.40 |
| 30.1319 | 341.92 | 0.1338 | 2.96593 | 1.26 |
| 34.7889 | 230.79 | 0.1338 | 2.57883 | 0.85 |
| 35.2675 | 321.78 | 0.0669 | 2.54492 | 1.19 |

Assignment of the $^{13}$C and $^{1}$H NMR spectra of PPB-enone is given in table 6 below.

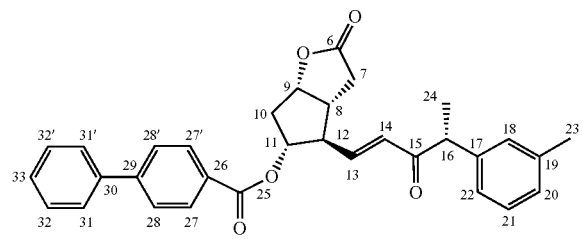 [SMILES: Cc1cccc([C@@H](C)C(=O)/C=C/[C@@H]2[C@H]3CC(=O)O[C@H]3C[C@H]2OC(=O)c2ccc(-c3ccccc3)cc2)c1]

Structure and Numbering of PPB-Enone as Used for NMR Data

TABLE 6

| Numbering | $^{13}$C (ppm) | $^{1}$H (ppm) | Number of $^{1}$H | Multiplicity | Coupling constant (Hz) (+/− 0.2 Hz) |
|---|---|---|---|---|---|
| 6 | 176.42 | — | — | | |
| 7 | 34.15 | β: 2.87* | 1 | m | |
| | | α: 2.40 | 1 | m | |
| 8 | 41.99 | 2.87* | 1 | m | |
| 9 | 83.00 | 5.055 | 1 | m (t/td) | $J_{8,9} \sim J_{9,10\beta} \sim 6.4$, $J_{9,10\alpha} \sim 1.5$ |
| 10 | 37.34 | β: 2.55$^{\&}$ | 1 | m (dt) | $J_{gem} \sim 15.1$, $J_{10\beta,11} = 6.4$ $J_{10\alpha,11} \sim 4.6$ |
| | | α: 2.05 | 1 | m (dd) | |
| 11 | 78.71 | 5.21 | 1 | m (td/q) | $J_{11,12} = 5.4$ |
| 12 | 53.13 | 2.95 | 1 | m (dt/ddd) | |
| 13 | 144.78$^{\$}$ | 6.815 | 1 | dd | $J_{13,14} = 15.7$; $J_{12,13} = 8.2$ |
| 14 | 129.54 | 6.27 | 1 | d | |
| 15 | 199.01 | — | — | — | |
| 16 | 49.27 | 4.10 | 1 | q | $J_{16,24} = 6.8$ |
| 17 | 140.44 | — | — | — | |
| 18 | 128.35$^{\$}$ | 7.01*** | 1 | m (s) | |
| 19 | 137.74 | — | — | — | |
| 20 | 127.44 | 6.97*** | 1 | m (d) | |
| 21 | 128.50 | 7.14 | 1 | m (t) | $J_{20,21} = J_{21,22} = 7.5$ |
| 22 | 124.88 | 7.00*** | 1 | m (d) | |
| 23 | 20.90 | 2.22 | 3 | m (s) | |
| 24 | 17.32 | 1.275 | 3 | d | |
| 25 | 164.82 | — | — | — | |
| 26 | 128.09 | — | — | — | |
| 27, 27' | 129.84 | 7.94$^{\#}$ | 2 | m (d) | $J_{26,27} = 8.2$ |
| 28, 28' | 126.79 | 7.80$^{\#\#\#}$ | 2 | m (d) | |
| 29 | 144.84$^{\$}$ | — | — | — | |
| 30 | 138.75 | — | — | — | |
| 31, 31' | 126.96 | 7.74$^{\#\#\#}$ | 2 | m (d) | $J_{31,32} = 7.5$ |
| 32, 32' | 129.06 | 7.51 | 2 | m (t) | |
| 33 | 128.41$^{\$}$ | 7.43 | 1 | m (t) | $J_{32,33} = 7.3$ |

$^{\$}$Partly overlapped $^{13}$C NMR signals.
*, , *, $^{\#\#\#}$Partly overlapped $^{1}$H NMR signals.
$^{\#}$Partly overlapped by the $^{1}$H NMR signals of the sample impurity.
$^{\&}$Overlapped $^{1}$H NMR signal of the DMSO solvent.

Example 4: Crystallization of 16-(S)-PPB-Enone (16-(S)-10)

[(3aR,4R,5R,6aS)-4-[(E,4S)-4-(m-tolyl)-3-oxo-pent-1-enyl]-2-oxo-3,3a,4,5,6,6a-hexahydrocyclopenta[b]furan-5-yl] 4-phenylbenzoate 10 g of $K_{r3}$ crystals prepared in Example 3.a (containing at least 85% 16-(S)-PPB-enone) were dissolved in 60 mL of dichloromethane, then 200 mL of tert-butyl methyl ether was added with stirring at room temperature. The precipitated crystals were filtered, washed, dried, and then the crystallization was repeated two more times. The product of the last crystallization (16-(S)-PPB-enone) contained less than 2% PPB-enone.

Yield: 6.4 g (64%), m.p.: 168.6-169.5° C.

Figure 7:
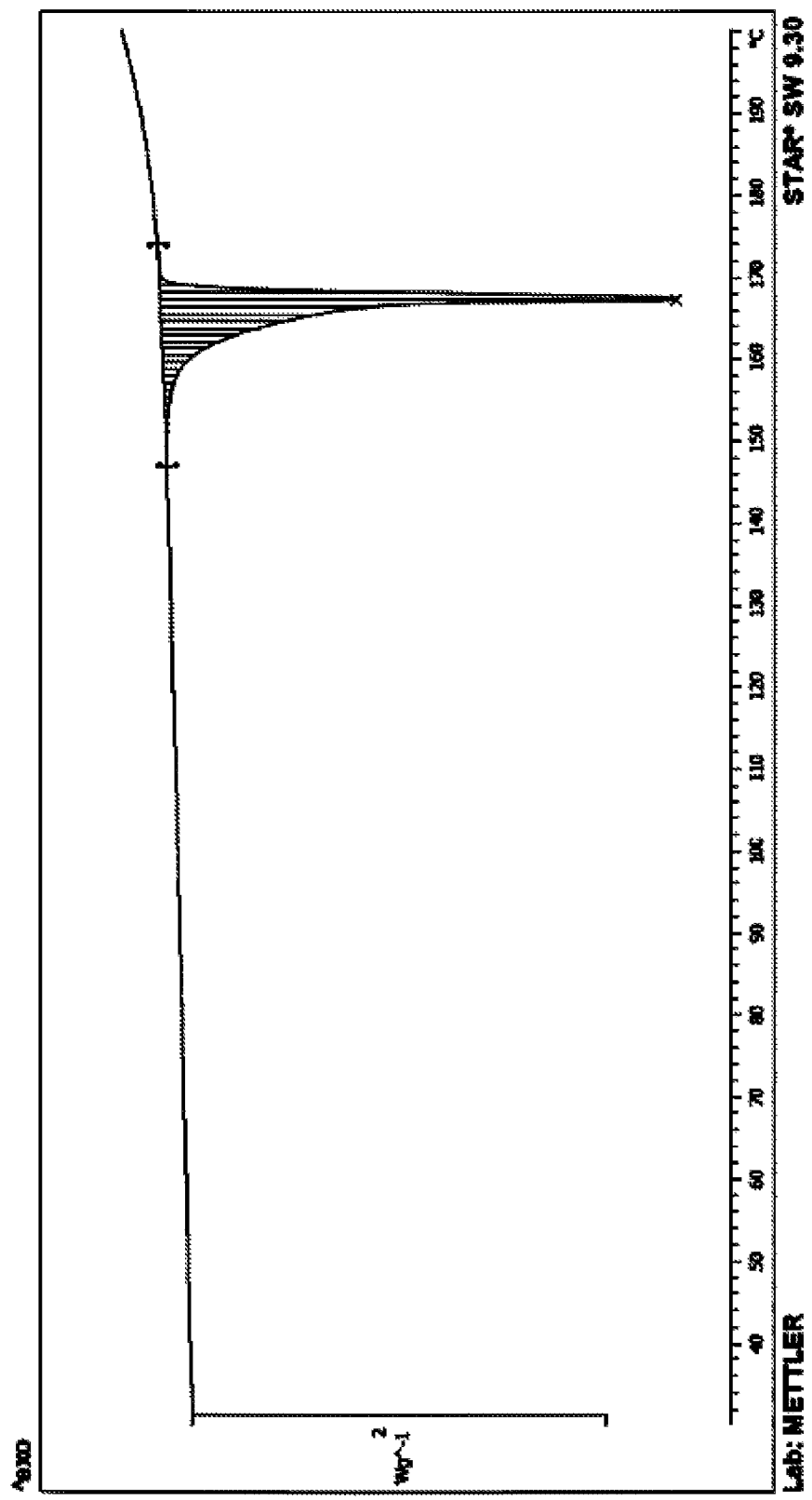
FIG. 7 shows a DSC curve of 16-(S)-PPB-enone prepared according to Example 4.

The DSC curve of 16-(S)-PPB-enone is shown in FIG. 7.

Figure 8:
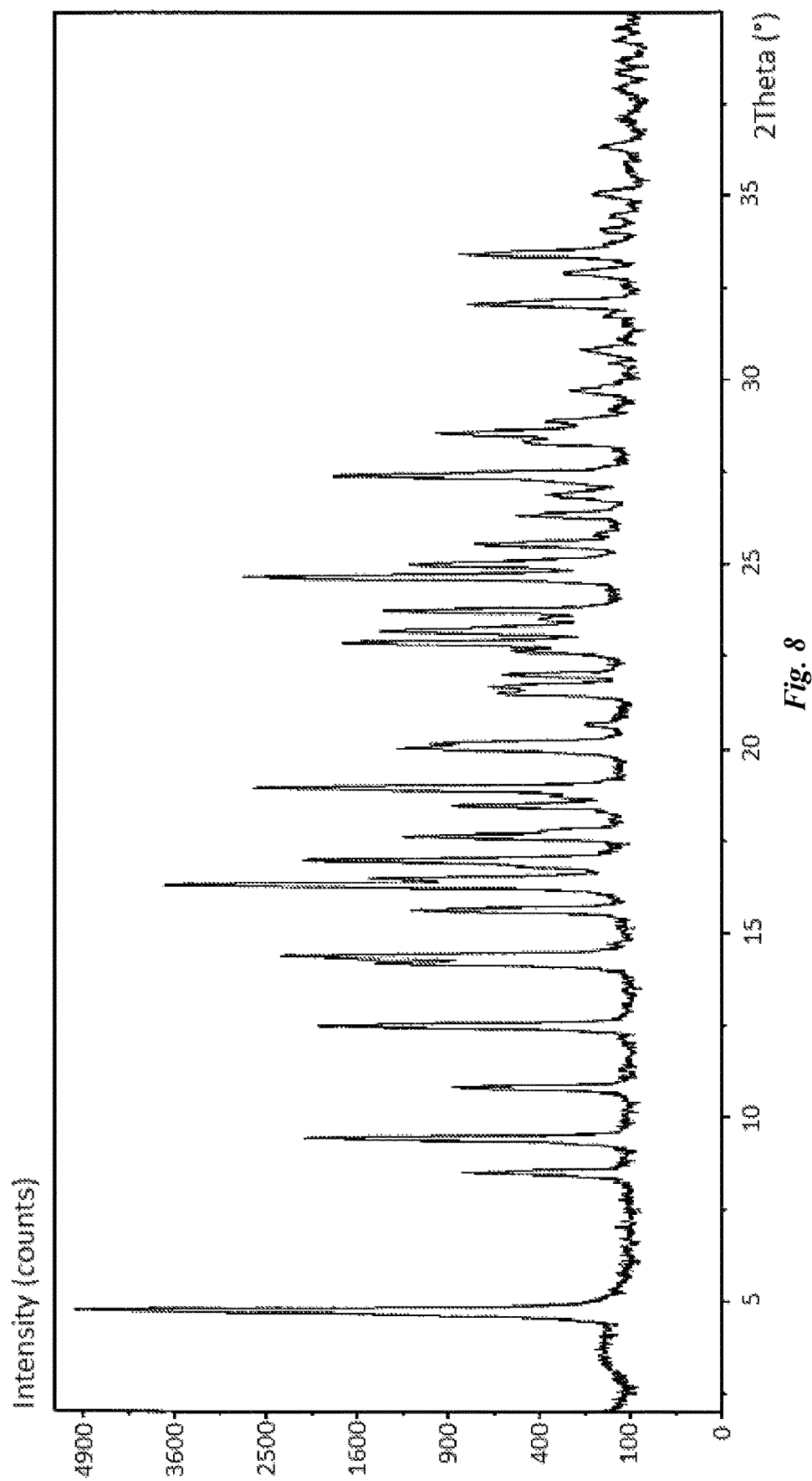
FIG. 8 shows a powder X-ray diffraction pattern of 16-(S)-PPB-enone prepared according to Example 4.

The powder X-ray diffraction pattern of 16-(S)-PPB-enone is shown in FIG. 8, the characteristic peaks are listed in Table 7 below.

TABLE 7

| Pos. [° 2Th.] | Height [cts] | FWHM [° 2Th.] | d-spacing [A] | Rel. Int. [%] |
|---|---|---|---|---|
| 4.7739 | 4889.23 | 0.1171 | 18.51062 | 100.00 |
| 8.4963 | 657.87 | 0.1004 | 10.40732 | 13.46 |
| 9.4335 | 1976.19 | 0.1171 | 9.37535 | 40.42 |
| 10.8115 | 762.60 | 0.1004 | 8.18337 | 15.60 |
| 12.4898 | 1841.08 | 0.1171 | 7.08723 | 37.66 |
| 14.1977 | 1324.69 | 0.0836 | 6.23827 | 27.09 |
| 14.3645 | 2211.67 | 0.1004 | 6.16624 | 45.24 |
| 15.6199 | 1040.57 | 0.1004 | 5.67333 | 21.28 |
| 16.3037 | 3620.72 | 0.1004 | 5.43691 | 74.06 |
| 16.4732 | 1361.49 | 0.0836 | 5.38133 | 27.85 |
| 16.9771 | 1981.96 | 0.1004 | 5.22273 | 40.54 |
| 17.6250 | 1109.30 | 0.0836 | 5.03218 | 22.69 |
| 18.4690 | 733.86 | 0.1004 | 4.80409 | 15.01 |
| 18.9393 | 2507.41 | 0.1004 | 4.68584 | 51.28 |
| 20.0236 | 1103.48 | 0.0669 | 4.43448 | 22.57 |
| 20.1816 | 771.71 | 0.1004 | 4.4001 | 15.78 |
| 21.5735 | 415.78 | 0.2676 | 4.11925 | 8.50 |
| 21.9853 | 458.53 | 0.1004 | 4.04302 | 9.38 |
| 22.6250 | 414.37 | 0.0836 | 3.93015 | 8.48 |
| 22.8484 | 1602.11 | 0.1004 | 3.89222 | 32.77 |
| 23.1730 | 1264.82 | 0.1004 | 3.83843 | 25.87 |
| 23.7181 | 1240.79 | 0.1171 | 3.75143 | 25.38 |
| 24.6352 | 2605.42 | 0.1338 | 3.61381 | 53.29 |
| 24.9754 | 1026.04 | 0.1506 | 3.56535 | 20.99 |
| 25.5301 | 612.59 | 0.1171 | 3.48913 | 12.53 |
| 26.3065 | 367.86 | 0.1171 | 3.38789 | 7.52 |
| 26.8660 | 209.01 | 0.2007 | 3.3186 | 4.27 |
| 27.3898 | 1672.40 | 0.1171 | 3.25631 | 34.21 |
| 28.5302 | 773.60 | 0.1004 | 3.12869 | 15.82 |
| 29.6954 | 161.02 | 0.1673 | 3.00852 | 3.29 |
| 30.8052 | 129.95 | 0.1673 | 2.90263 | 2.66 |
| 32.0607 | 639.68 | 0.1171 | 2.79177 | 13.08 |
| 32.9067 | 197.58 | 0.1673 | 2.72191 | 4.04 |
| 33.4029 | 711.91 | 0.1171 | 2.68259 | 14.56 |

Assignment of the $^{13}$C and $^{1}$H NMR spectra of 16-(S)-PPB-enone is given in table 8 below.

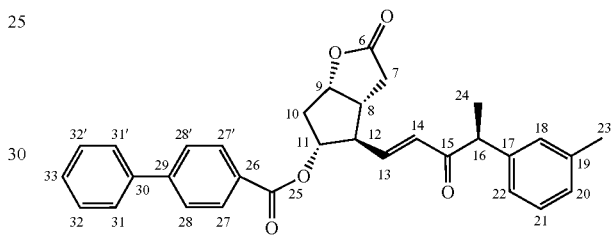

Structure and Numbering of 16-(S)-PPB-Enone as Used for NMR Data

TABLE 8

| Numbering | $^{13}$C (ppm) | $^{1}$H (ppm) | Number of $^{1}$H | Multiplicity | Coupling constant (Hz) (+/− 0.2 Hz) |
|---|---|---|---|---|---|
| 6 | 176.41 | — | — | | |
| 7 | 34.16 | β: 2.875* | 1 | m | |
|  |  | α: 2.42** | 1 | m | |
| 8 | 42.00 | 2.865* | 1 | m | |
| 9 | 82.95$ | 5.055 | 1 | td | $J_{8,9} = 6.2$; $J_{9,10\alpha} = 1.5$ |
| 10 | 37.36 | β: 2.57 | 1 | dt | $J_{gem} = 15.1$, |
|  |  | α: 2.045*** | 1 | m (ddd) | $J_{9,10\beta} = J_{10\beta,11} = 6.6$ |
|  |  |  |  |  | $J_{10\alpha,11} = 4.8$ |
| 11 | 78.64$ | 5.21 | 1 | m (td/q) | $J_{11,12} = 5.6$ |
| 12 | 53.17$ | 2.935* | 1 | m (dt/ddd) | $J_{8,12} = 6.9$ |
| 13 | 144.58 | 6.81+ | 1 | dd | $J_{13,14} = 15.7$; |
|  |  |  |  |  | $J_{12,13} = 8.2$ |
| 14 | 129.57$ | 6.29++ | 1 | d | |
| 15 | 198.90 | — | — | | |
| 16 | 49.50 | 4.09 | 1 | q | $J_{16,24} = 6.8$ |
| 17 | 140.39$ | — | — | | |
| 18 | 128.36$$ | 7.00+++ | 1 | m (s) | |
| 19 | 137.72 | — | — | | |
| 20 | 127.42 | 6.97+++ | 1 | m (d) | |
| 21 | 128.48$$ | 7.125 | 1 | m (t) | $J_{20,21} = J_{21,22} = 7.5$ |
| 22 | 124.92$ | 6.99+++ | 1 | m (d) | |
| 23 | 20.89 | 2.205# | 3 | m (s) | |
| 24 | 17.38$ | 1.27## | 3 | d | |
| 25 | 164.81 | — | — | | |
| 26 | 128.08 | — | — | | |
| 27, 27' | 129.81$ | 7.93### | 2 | m (d) | $J_{26,27} = 8.3$ |
| 28, 28' | 126.78 | 7.785& | 2 | m (d) | |

TABLE 8-continued

| Numbering | $^{13}$C (ppm) | $^1$H (ppm) | Number of $^1$H | Multiplicity | Coupling constant (Hz) (+/− 0.2 Hz) |
|---|---|---|---|---|---|
| 29 | 144.83$^\$$ | — | — | — | |
| 30 | 138.75 | — | — | — | |
| 31, 31' | 126.95 | 7.745$^\&$ | 2 | m (d) | $J_{31,32} = 7.5$ |
| 32, 32' | 129.08 | 7.515 | 2 | m (t) | |
| 33 | 128.41$^{\$\$}$ | 7.435 | 1 | m (t) | $J_{32,33} = 7.3$ |

$^\$$Partly overlapped by the $^{13}$C NMR signals of the PPB-IP-enone.
$^{\$\$}$Partly overlapped $^{13}$C NMR signals.
$^*$, $^{+++}$, $^\&$Partly overlapped $^1$H NMR signals.
$^{}$, $^{*}$, $^+$, $^{++}$, $^\#$, $^{\#\#\#}$, $^\&$Partly overlapped by the $^1$H NMR signal of the PPB-IP-enone impurity.
$^{\#\#}$Partly overlapped by the $^1$H NMR signals of the unknown impurities.

Example 5: Epimerization of 16-(S)-PPB-Enone (16-(S)-10), Followed by Preparation of PPB-Enone from the Mixture by Fractional Crystallization According to Example 3.a

Example 5.1

5.000 g of 16-(S)-PPB-enone (16-(S)-10) obtained as K$_{r3}$ in Example 3.a was dissolved in 100 mL of ethyl acetate, then 5.0 g of silica gel and 2.50 mL of triethylamine were added thereto, and stirred at 55-65° C. for about 23 hours. At the end of the reaction, the isomer ratio was approximately 1:1 and 10-15% by-product was formed. The reaction mixture was then cooled, filtered, and the crystals were washed with ethyl acetate, and the combined filtrate was evaporated. The evaporation residue was fractionally crystallized as described in Example 3.a to give PPB-enone (16-(R)-10).

Yield of PPB-enone: 1.442 g (29%; calculated based on 16-(S)-PPB-enone (Kr$_3$), 14.5% calculated based on the starting 16-(R,S)-PPB-enone).

Example 5.2

5.000 g of 16-(S)-PPB-enone (16-(S)-10) obtained as K$_{r3}$ in Example 3.a was dissolved in 150 mL of ethyl acetate, 75.0 g of aluminium oxide was added thereto, then it was stirred at 20-25° C. for about 1.5 hours. At the end of the reaction, the isomer ratio was approximately 1:1 and 10-15% by-product was formed. The reaction mixture was then cooled, filtered, and the crystals were washed with ethyl acetate, and the combined filtrate was evaporated. The evaporation residue was fractionally crystallized as described in Example 3.a to give PPB-enone (16-(R)-10).

Yield: 0.865 g (17%; calculated based on 16-(S)-PPB-enone, 8.5%; calculated based on 16-(R,S)-PPB-enone).

Example 5.3

5.000 g of 16-(S)-PPB-enone (16-(S)-10) obtained as K$_{r3}$ in Example 3.a was dissolved in 100 mL of toluene, a solution of 0.500 g of pTsOH·H$_2$O in 2.5 mL of tetrahydrofuran was added thereto, then it was stirred at 65-75° C. for about 15-20 hours. At the end of the reaction, the isomer ratio was approximately 1:1 and about 5% by-product was formed. The reaction mixture was then cooled and neutralized with 0.422 mL of triethylamine. The precipitate was filtered, and the crystals were washed with toluene, and the combined filtrate was evaporated. The evaporation residue was fractionally crystallized as described in Example 3.a to give PPB-enone (16-(R)-10).

Yield: 1.698 g (34%; calculated based on 16-(S)-PPB-enone, 17%; calcd. for 16-(R,S)-PPB-enone).

Example 5.4

57.771 g of 16-(S)-PPB-enone (16-(S)-10) obtained as K$_{r3}$ in Example 3.a was dissolved in 1155 mL of ethyl acetate, 28.8 g of silica gel and 57.7 ml of triethylamine were added thereto, then it was stirred at 55-65° C. for about 12 hours. At the end of the reaction, the isomer ratio was approximately 1:1 and 10-15% by-product was formed. The reaction mixture was then cooled, filtered, and the crystals were washed with ethyl acetate, and the combined filtrate was evaporated. The evaporation residue was fractionally crystallized as described in Example 3.a to give PPB-enone (16-(R)-10).

Yield: 20.10 g (34.8%; calculated based on 16-(S)-PPB-enone, 17.4%; calculated based on 16-(R,S)-PPB-enone).

The resulting PPB-enone (16-(R)-10) crystals can be recrystallized from a mixture of tert-butyl methyl ether: dichloromethane=5:1 as described in Example 3.a.

Yield: 19.70 g (98%).

Example 6, Reduction of PPB-Enone

Reduction of the 15-Oxo Group

[(3aR,4R,5R,6aS)-4-[(E,4R)-3-hydroxy-4-(m-tolyl)pent-1-enyl]-2-oxo-3,3a,4,5,6,6a-hexahydrocyclopenta[b]furan-5-yl] 4-phenylbenzoate

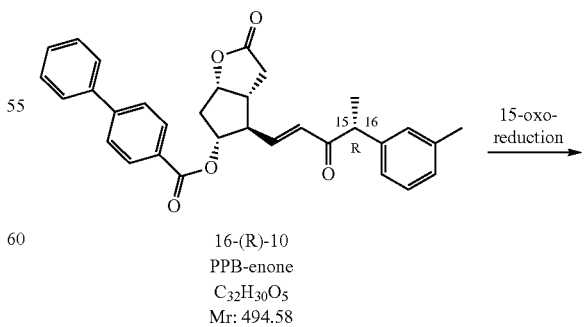

16-(R)-10
PPB-enone
C$_{32}$H$_{30}$O$_5$
Mr: 494.58

43

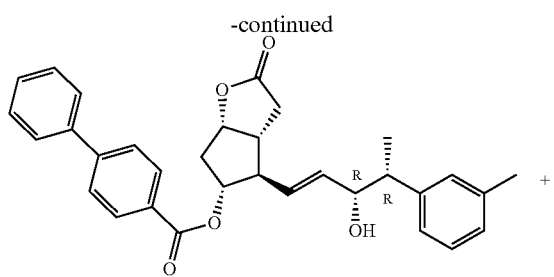

15-(R), 16-(R)-11
PPB-enol
$C_{32}H_{32}O_5$
Mr: 496.59

+

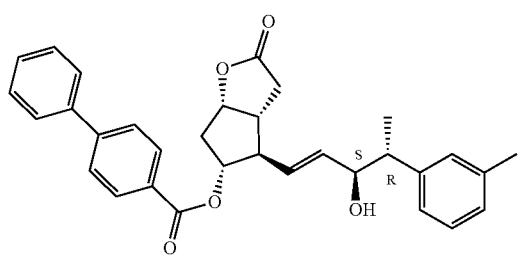

15-(S), 16-(R)-11
15-(S)-PPB-enol
$C_{32}H_{32}O_5$
Mr: 496.59

Reduction with Sodium Borohydride in the Presence of Silica Gel:

1.51 kg of PPB-enone (16-(R)-10) were dissolved in 13.7 L of dichloromethane, 2.04 kg of silica gel were added and the suspension was cooled to 0±5° C. under an inert atmosphere. Under vigorous stirring, a solution of 0.183 kg of sodium borohydride in 340 mL of water was added. The reaction mixture was stirred while maintaining the temperature. After stirring for 1 hour, 270 mL of methanol was added. After the reduction was complete (about 5-8 hours), a solution of 515 mL of concentrated hydrochloric acid in 2.05 L of water was carefully added at 0±5° C., then, after ceasing cooling, 1.36 L of methanol was added. After stirring for about 20 minutes, the reaction mixture was filtered, the filtered solid was washed with dichloromethane: methanol=5:1, the combined filtrate was stirred well, and the phases were separated. The organic layer was washed with water and then with a saturated sodium chloride solution, dried over sodium sulphate, then the desiccant was filtered off, washed and evaporated.

Yield 1.52 kg (100%), sticky oil. Isomer ratio:PPB-enol: 15-(S)-PPB-enol=6:4.

44

Example 7, Removal of the PPB Protecting Group (3aR,4R,5R,6aS)-5-hydroxy-4-[(E,3R,4R)-3-hydroxy-4-(m-tolyl)pent-1-enyl]-3,3a,4,5,6,6a-hexahydrocyclopenta[b]furan-2-one

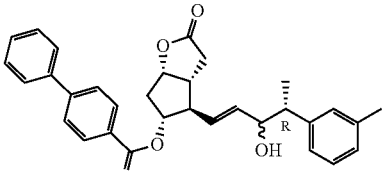

15-(R,S), 16-(R)-11
15-(R,S)-PPB-enol
$C_{32}H_{32}O_5$
Mr: 496.59 removal of protecting group
chromathography
crystallization
(optional)

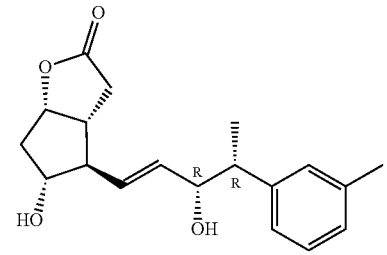

Hydroxyenol
$C_{19}H_{24}O_4$
Mr: 316.39

1.36 kg of PPB-enol (15-(R,S), 16-(R)-11) of Example 6 was dissolved in 4.9 L of distilled methanol at 40-45° C., and 0.38 kg of potassium carbonate was added. While maintaining the temperature, the reaction mixture was stirred for one hour, then it was cooled to 0-5° C., and 4.28 L of 1 M hydrochloric acid solution was added. While maintaining the temperature, stirring was continued for one hour, then the precipitated crystals were filtered off and washed with a methanol-water mixture. 3.62 L of 1 M hydrochloric acid was added to the combined filtrate, and it was stirred at room temperature for 30-45 minutes. Upon completion of the stirring, the reaction mixture was concentrated under reduced pressure. The concentrated solution was extracted with 2×10 L of dichloromethane, the combined organic phase was washed with 1 M sodium hydrogen carbonate, the washing solution was extracted with 5 L of dichloromethane, the combined organic phase was washed with a saturated sodium chloride solution, dried over sodium sulphate, the desiccant was filtered off, washed with dichloromethane, and the washing liquid was added to the organic phase. The combined organic phase was concentrated (to about 3.5 kg) under reduced pressure.

The evaporated concentrate was purified by chromatography on a silica gel column prepared with a dichloromethane:acetone=7:1 solvent mixture, using dichloromethane:acetone=7:1 and thereafter dichloromethane:acetone=2:1 solvent mixtures as eluent. The product-containing fractions were combined, and concentrated under reduced pressure.

Yield: 415.93 g (48%) thick oil.

The evaporation residue is preferably crystallized.

To do this, the evaporation residue was dissolved in tert-butyl methyl ether using a bath at 40-50° C., then cooled to 0-5° C. with stirring. After crystallization began, the crystal suspension was stirred for an additional 25-35 minutes and the crystallization was completed by addition of diisopropyl ether. The mixture containing the precipitated crystals was stirred for an additional 1 hour, while maintaining the temperature.

The crystals were filtered, washed and dried at room temperature to constant weight.

Yield: 303.6 g (73% for the crystallization step), colourless crystal.

Although the compound itself is known e.g. from the patent applications Nos. WO 2010029925 A1 and WO 2011111714 A1, the crystalline form of the compound has not been described nor characterized therein.

The crystalline form is characterized by a melting point of 72.5-73.4° C. and an optical rotation of $[\alpha]_D=25°$ (in a 1% ethanolic solution, measured at 20° C.).

Figure 9:
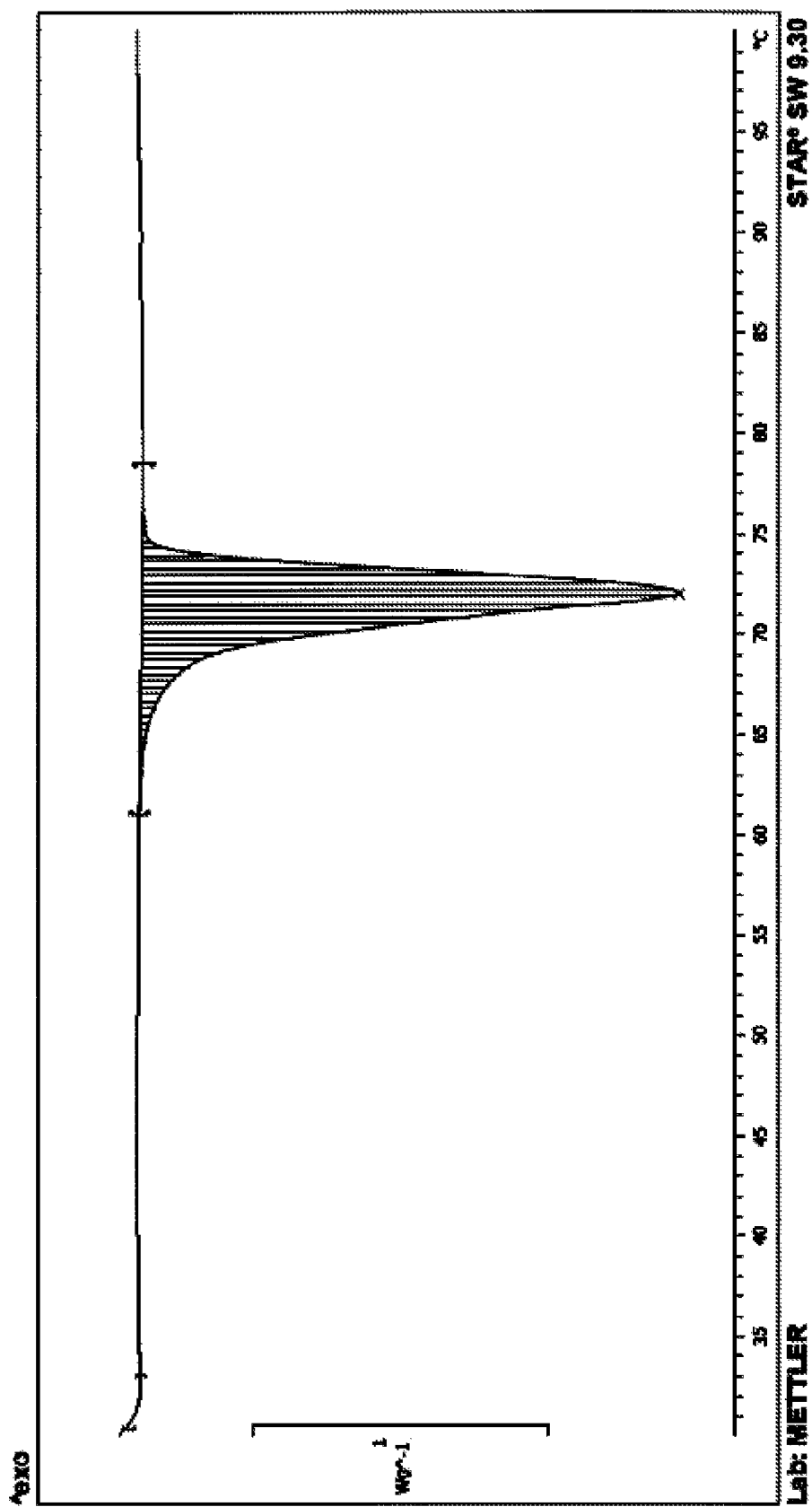
FIG. 9 shows a DSC curve of crystalline hydroxyenol prepared according to Example 7.

The DSC curve of the crystalline hydroxyenol is shown in FIG. 9.

Figure 10:
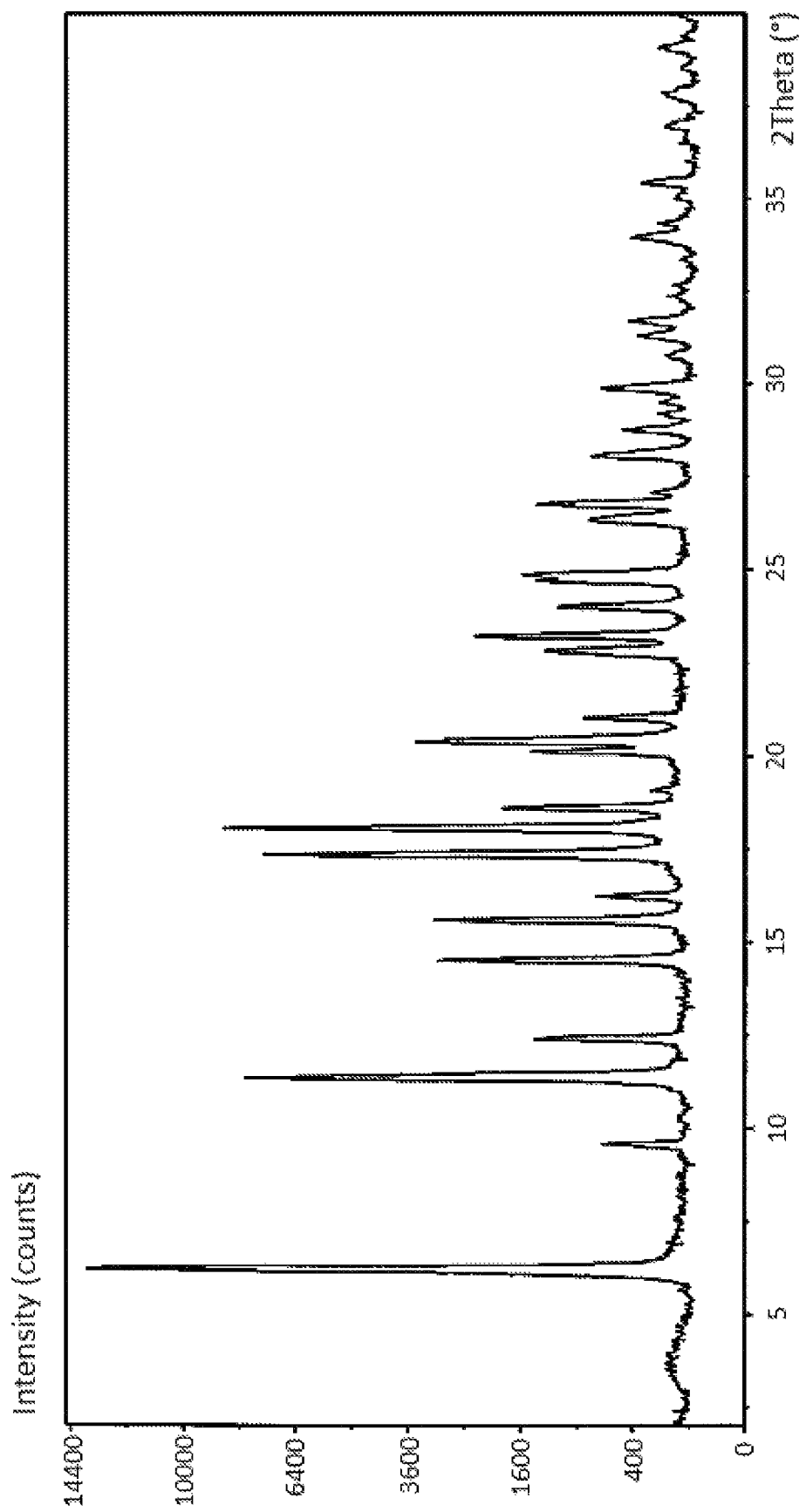
FIG. 10 shows a powder X-ray diffraction pattern of crystalline hydroxyenol prepared according to Example 7.

The powder X-ray diffraction pattern of hydroxyenol is shown in FIG. 10, the characteristic peaks are listed in Table 9 below.

TABLE 9

| Pos. [° 2Th.] | Height [cts] | FWHM [° 2Th.] | d-spacing [Å] | Rel. Int. [%] |
| --- | --- | --- | --- | --- |
| 6.2270 | 13562.79 | 0.1171 | 14.19406 | 100.00 |
| 9.5599 | 526.11 | 0.1004 | 9.25169 | 3.88 |
| 11.3561 | 7691.46 | 0.1338 | 7.79205 | 56.71 |
| 12.4016 | 1252.64 | 0.1171 | 7.13745 | 9.24 |
| 14.5196 | 2836.38 | 0.1004 | 6.10072 | 20.91 |
| 15.5914 | 2895.00 | 0.1171 | 5.68365 | 21.35 |
| 16.2348 | 567.08 | 0.1004 | 5.45983 | 4.18 |
| 17.3603 | 7089.03 | 0.1338 | 5.1083 | 52.27 |
| 18.0703 | 8356.01 | 0.1004 | 4.90916 | 61.61 |
| 18.6125 | 1714.30 | 0.1338 | 4.76737 | 12.64 |
| 20.1339 | 1251.75 | 0.1004 | 4.41042 | 9.23 |
| 20.4002 | 3290.52 | 0.1171 | 4.35346 | 24.26 |

TABLE 9-continued

| Pos. [° 2Th.] | Height [cts] | FWHM [° 2Th.] | d-spacing [Å] | Rel. Int. [%] |
| --- | --- | --- | --- | --- |
| 21.0061 | 691.95 | 0.1171 | 4.22922 | 5.10 |
| 22.8112 | 1134.82 | 0.1338 | 3.89848 | 8.37 |
| 23.2096 | 2183.39 | 0.1171 | 3.83246 | 16.10 |
| 23.9972 | 985.62 | 0.1338 | 3.70842 | 7.27 |
| 24.7051 | 1219.39 | 0.0836 | 3.60375 | 8.99 |
| 24.8622 | 1417.03 | 0.1171 | 3.58134 | 10.45 |
| 26.3355 | 641.00 | 0.2007 | 3.38423 | 4.73 |
| 26.7606 | 1252.39 | 0.1338 | 3.33143 | 9.23 |
| 28.0592 | 626.05 | 0.1338 | 3.18013 | 4.62 |
| 28.7617 | 339.28 | 0.1338 | 3.10403 | 2.50 |
| 29.8764 | 542.33 | 0.1338 | 2.99072 | 4.00 |
| 31.2965 | 257.45 | 0.1338 | 2.85817 | 1.90 |
| 31.6923 | 328.52 | 0.1338 | 2.82337 | 2.42 |
| 33.9579 | 290.14 | 0.1673 | 2.64001 | 2.14 |
| 35.4194 | 238.12 | 0.1338 | 2.53436 | 1.76 |
| 37.8054 | 116.65 | 0.2676 | 2.37972 | 0.86 |

Assignment of the $^{13}$C and $^1$H NMR spectra of hydroxyenol are shown in Table 10 below.

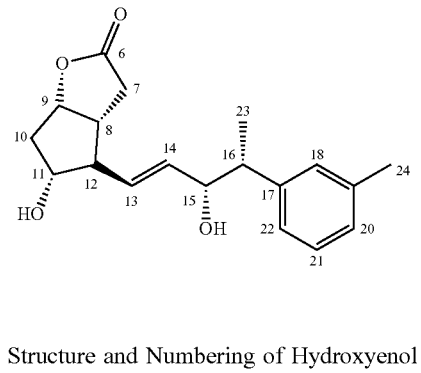

Structure and Numbering of Hydroxyenol

TABLE 10

| Numbering | $^{13}$C (ppm) | $^1$H (ppm) | Number of $^1$H | Multiplicity | Coupling constant (Hz) (+/− 0.3 Hz) |
| --- | --- | --- | --- | --- | --- |
| 6 | 176.76 | — | — | — | |
| 7 | 34.08 | 7β: 2.57* | 1 | m (dd) | $J_{7gem} = 18.0$, |
| | | 7α: 2.02** | 1 | m (dd) | $J_{7β,8} = 10.0$ |
| | | | | | $J_{7α,8} = 2.2$ |
| 8 | 41.56 | 2.31*** | 1 | m (dtd) | $J_{8,9} = J_{8,12} = 7.5$ |
| 9 | 82.64 | 4.76$^+$ | 1 | m (td) | $J_{9,10α} = 2.5$ |
| 10 | 39.76 | 10β: 2.09** | 1 | m (dt) | $J_{9,10β} = J_{10β,11} = 6.7$ |
| | | 10α: 1.585 | 1 | ddd | $J_{10gem} = 14.4$, |
| | | | | | $J_{10α,11} = 6.3$ |
| 11 | 75.78$^\$$ | 3.655 | 1 | dddd (qd) | |
| 11-OH | | 4.78$^+$ | 1 | m (d) | $J_{11,11\text{-}OH}$~5.0 |
| 12 | 55.33 | 2.05** | 1 | m (q) | $J_{11,12}$~7.2 |
| 13 | 130.00 | 5.20 | 1 | dd | $J_{13,14} = 1.5.5$; |
| | | | | | $J_{12,13} = 7.0$ |
| 14 | 134.00 | 5.26 | 1 | dd | $J_{14,15} = 6.3$ |
| 15 | 75.78 | 3.93 | 1 | q (td) | |
| 15-OH | | 4.78$^+$ | 1 | m (d) | $J_{15,15\text{-}OH}$~5.1 |
| 16 | 46.00 | 2.61* | 1 | m (qui) | $J_{15,16} = J_{16,23} = 7.0$ |
| 17 | 144.61 | — | — | — | |
| 18 | 128.78 | 6.965$^{++}$ | 1 | m (s) | |
| 19 | 136.70 | — | — | — | |

TABLE 10-continued

| Numbering | $^{13}C$ (ppm) | $^{1}H$ (ppm) | Number of $^{1}H$ | Multiplicity | Coupling constant (Hz) (+/- 0.3 Hz) |
|---|---|---|---|---|---|
| 20 | 126.40 | 6.96++ | 1 | m (d) | |
| 21 | 127.71 | 7.125 | 1 | t | $J_{20,21} = J_{21,22} = 7.4$ |
| 22 | 125.00 | 6.945++ | 1 | m (d) | |
| 23 | 17.40 | 1.21 | 3 | d | |
| 24 | 21.05 | 2.265*** | 3 | m (s) | |

$ Partly overlapped $^{13}C$ NMR signals.
*, , *, +, ++Partly overlapped $^{1}H$ NMR signals

Example 8, Preparation of the Racemic Phosphonate (2-Oxo-3-m-tolyl-butyl)-phosphonic acid dimethyl ester

Example 8.1, Route A

Starting material: methylphenylacetic acid
Reaction steps: alkylation (methylation)
esterification (formation of methyl ester)
phosphonate formation

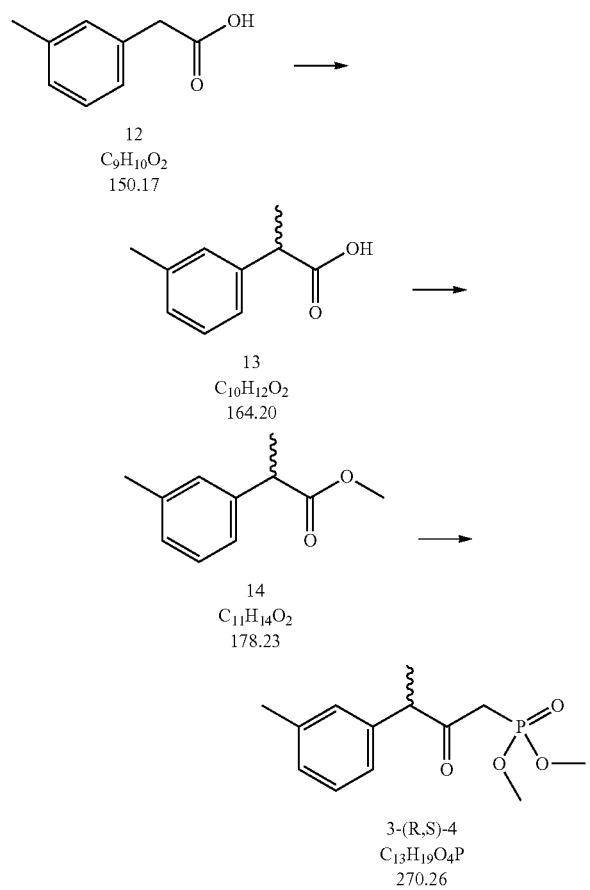

12
$C_9H_{10}O_2$
150.17

13
$C_{10}H_{12}O_2$
164.20

14
$C_{11}H_{14}O_2$
178.23

3-(R,S)-4
$C_{13}H_{19}O_4P$
270.26

8.1.1. Preparation of methylphenylpropionic acid (13)
a.) Base: Butyl Lithium
4.31 kg of methylphenylacetic acid (12) was dissolved in 38.0 kg of anhydrous tetrahydrofuran. Under an inert atmosphere, the reaction mixture was cooled to −60 to −75° C., and 26.2 kg of a 15% butyl lithium solution was added. After the addition, the reaction mixture was stirred for further 15 minutes, and then 805 mL of diisopropylamine (DIPA) was added while maintaining the temperature. After stirring for 15 minutes, the reaction mixture was heated to −30° C., and 3.60 L of methyl iodide was added. The cooling was stopped and, after stirring for 10 min, the reaction mixture was charged onto 98 L of a 1 M sodium hydrogen sulphate. After settling, the phases were separated, and the aqueous phase was extracted with tert-butyl methyl ether. The combined organic phase was washed with saturated sodium chloride solution (3×32 kg), and at the first washing step, 81.8 g of sodium pyrosulfite was also added into the mixture. The organic layer was dried over sodium sulphate, the desiccant was filtered off, washed and the filtrate was evaporated under reduced pressure.
Yield: 4.62 kg (98%), orange liquid.

8.1.2. Preparation of Methylphenylpropionic Acid (13)
b.) Base: Lithium diisopropylamide (LDA)
Preparation of LDA Solution:
187 mL of diisopropylamine was dissolved in 300 mL of anhydrous tetrahydrofuran. Under an inert atmosphere, the solution was cooled to −20° C., then 511 mL of a 2.5 M butyl lithium solution was added. The reaction mixture was stirred for 2 hours at −10° C.
Alkylation:
80 g of methylphenylacetic acid (12) was dissolved in 800 mL of anhydrous tetrahydrofuran. Under an inert atmosphere, the solution was cooled to −20° C., then, while maintaining the temperature, the prepared LDA solution was added thereto. The reaction mixture was stirred at −10° C. for 30 minutes, then 40 mL of methyl iodide was added at −20 to −10° C. After the addition, the reaction mixture was stirred at 0° C. for 30 minutes. The reaction mixture was then quenched with 1200 mL of a 2 M sodium hydrogen sulphate solution, and after vigorous mixing the phases were separated. The aqueous phase was extracted with tert-butyl methyl ether. The combined organic phase was washed with saturated sodium chloride solution twice, and at the first washing step, 1.52 g of sodium pyrosulphite was also added to the mixture. The organic layer was dried over sodium sulphate, the desiccant was filtered off, washed and the filtrate was evaporated under reduced pressure.
Yield: 87.5 g (100%), orange liquid.

8.1.3. Preparation of Methylphenylpropionic Acid Methyl Ester (14)
a.) Esterification Using Hydrochloric Acid
4.60 kg of methylphenylpropionic acid (13) was dissolved in 35 kg of distilled methanol, 350 ml of concentrated hydrochloric acid was added and it was stirred at room temperature. After reaching the desired conversion (about 12 hours), 1.17 L of triethylamine was added to the reaction mixture, then at atmospheric pressure, it was concentrated to about 15 L. 40 kg of toluene was added and after vigorous stirring the aqueous phase was separated. The organic phase was washed with saturated sodium chloride solution, dried over sodium sulphate, the desiccant was filtered off, washed with toluene and the filtrate was evaporated under reduced pressure.

Yield: 4.74 kg (95%), yellow liquid.

8.1.4. Preparation of Methylphenylpropionic Acid Methyl Ester (14)

b.) Esterification Using Sulphuric Acid 4.60 kg of methylphenylpropionic acid (13) was dissolved in 36 kg of distilled methanol, 225 ml of concentrated sulphuric acid was added and it was stirred at 20-25° C. After 1 hour, with vigorous stirring, 890 g of sodium carbonate was added to the reaction mixture, then under reduced pressure, it was concentrated to about 4.6 kg. 32 kg of tert-butyl methyl ether was added to the concentrate, it was washed three times with 10% sodium carbonate solution, and the combined aqueous phase was extracted once with tert-butyl methyl ether, the combined organic phase was dried over sodium sulphate, the desiccant was filtered off, washed, and the combined filtrate was evaporated.

Yield: 3.25 kg (65%), yellow liquid.

8.1.5. Preparation of Racemic Phosphonate (3-(R,S)-4)

a.) Base: Butyl Lithium 23.8 kg of a 15% butyl lithium solution was added, under an inert atmosphere, to 49 kg of distilled toluene, after which the reaction mixture was cooled to −75 to −85° C. and, while maintaining the temperature, a solution of 8.25 kg of dimethyl methylphosphonate (DMMP) in 24 kg of distilled toluene was added. The reaction mixture was stirred for 30 minutes while maintaining the temperature, then, at −75 to −85° C., a solution of 4.74 kg of methylphenylpropionic acid methyl ester (14) in 20 kg of distilled toluene was added. After stirring for 30 minutes, the reaction mixture was charged onto a mixture of 70 L of a 1 M sodium hydrogen sulphate solution and 13 L of a saturated sodium chloride solution. The mixture was stirred at room temperature for 30 minutes, after settling the phases were separated and the aqueous phase was extracted with 2×20 L of toluene, the combined organic phase was washed with saturated sodium chloride solution, and it was dried over sodium sulphate. The desiccant was filtered off, washed and the combined filtrate was evaporated under reduced pressure.

Yield: 6.83 kg (95%), pale yellow oil.

8.1.6. Preparation of Racemic Phosphonate (3-(R,S)-4)

b.) Base: LDA

Preparation of LDA Solution:

A solution of 13.9 mL of diisopropylamine in 45 mL of anhydrous tetrahydrofuran was cooled to 0° C. under an inert atmosphere, and 54 mL of a butyl lithium solution (1.6 M in hexane) was added dropwise. After the addition, it was stirred for 20 minutes.

Phosphonate Formation:

To a solution of 6.36 g of methylphenylpropionic acid methyl ester (14) in 64 ml of anhydrous tetrahydrofuran, under an inert atmosphere, 37.7 ml of dimethyl methylphosphonate was added. The prepared LDA solution was added dropwise at 0° C. After 5-10 minutes of poststirring, the reaction mixture was acidified with a 5N hydrochloric acid (pH=2-3) under vigorous stirring, and the phases were separated, the aqueous phase was extracted with ethyl acetate, the organic phase was washed with water and with saturated sodium chloride solution, it was dried over sodium sulphate, the desiccant was filtered off, washed, and the combined filtrate was evaporated. Yield: 8.91 g (92.4%).

Example 8.2, Route B

Starting material: methylphenylacetic acid
Reaction steps: esterification (formation of methyl ether)
alkylation (methylation)
phosphonate formation

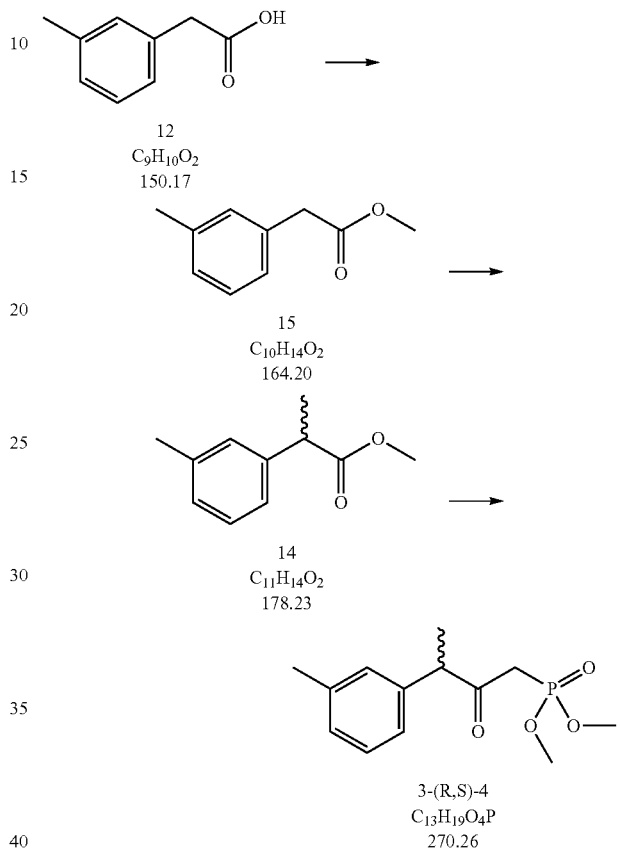

Preparation of Methylphenylacetic Acid Methyl Ester (15)

31.74 g of methylphenylacetic acid (12) was dissolved in 315 ml of methanol. While stirring at room temperature, 1.8 mL of conc. sulphuric acid was added thereto. After completion of the reaction (2-3 hours), the reaction mixture was concentrated under reduced pressure, the residue was dissolved in 210 mL of dichloromethane, washed with 1 M sodium hydrogen carbonate solution and then with saturated brine, dried over sodium sulphate, the desiccant was filtered off, washed, and the combined filtrate was evaporated.

Yield: 34.11 g (98.3%) oil.

Preparation of Methylphenylpropionic Acid Methyl Ester (14)

19.2 mL of diisopropylamine was dissolved in 345 mL of anhydrous tetrahydrofuran. Under an inert atmosphere, it was cooled to −60° C. and 85.9 mL of a 1.6 M solution of butyl lithium in hexane was added dropwise while stirring. After 10 minutes of poststirring, a solution of 15.01 g of methylphenylacetic acid methyl ester (15) in 16 ml of anhydrous tetrahydrofuran was added dropwise to the reaction mixture. After 10 minutes of poststirring, 15 mL of methyl iodide was added. After stirring for 15 minutes, the reaction mixture was poured onto 340 mL of a 2N hydrochloric acid. The phases were separated, the aqueous phase was extracted with diisopropyl ether, the organic phase was washed with 1 M sodium hydrogen carbonate solution, then with saturated brine, dried over sodium sulphate, the desiccant was filtered off, washed, and the combined filtrate was evaporated.

Yield: 16.21 g (99.5%).

The invention claimed is:

1. A process for the preparation of a compound of formula 1,

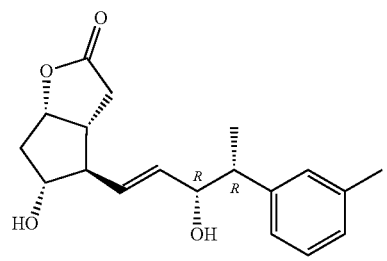

comprising the steps of:

separating a compound of formula 16-(R,S)-10 into its diastereomers 16-(R)-10 and 16-(S)-10 by fractional crystallisation,

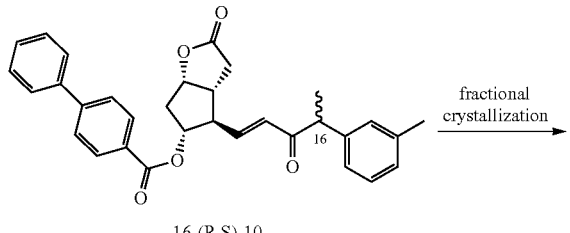

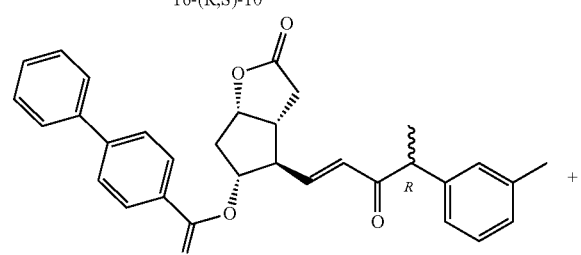

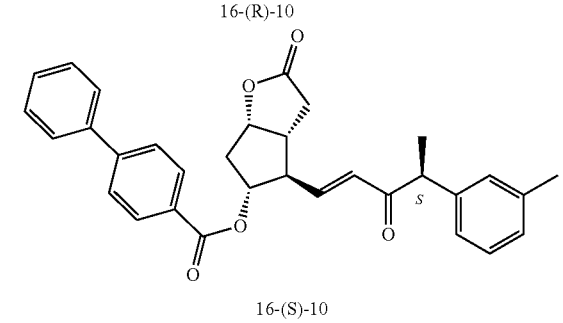

reducing the 15-oxo group of the compound of formula 16-(R)-10, thereby obtaining a compound of formula 15-(R,S), 16-(R)-11,

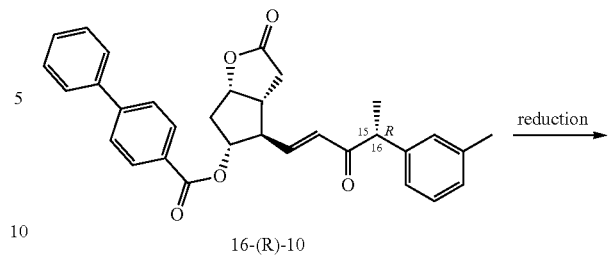

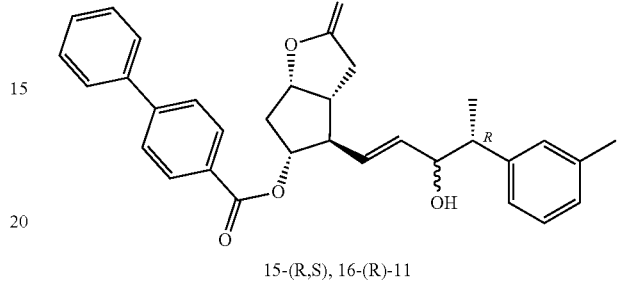

removing the protecting group of the compound of formula 15-(R,S), 16-(R)-11, isolating the compound of formula 1,

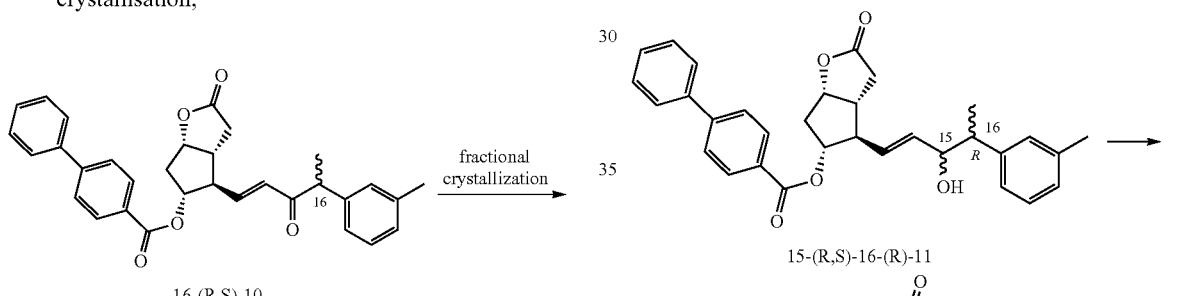

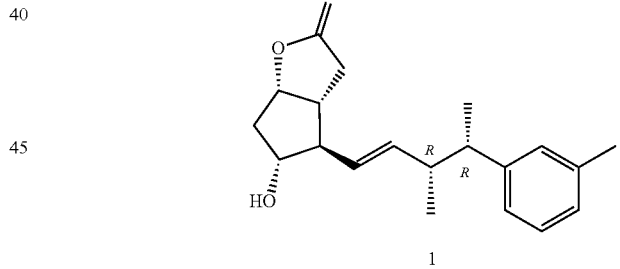

and optionally, crystallizing the compound of formula 1.

2. A process according to claim 1, wherein the solvent used for the fractional crystallization of the compound of formula 16-(R,S)-10 is selected from $C_{1-3}$ alcohols, tert-butyl methyl ether and their mixtures.

3. A process according to claim 2, wherein the fractional crystallization of the compound of formula 16-(R,S)-10 comprises (a) suspending the compound of formula 16-(R,S)-10 in the solvent, refluxing the suspension, followed by cooling the mixture to 25-35° C. and stirring while maintaining the temperature, followed by filtering, washing and drying the precipitated crystals, thereby obtaining crystals $K_{r1}$;

(b) seeding the filtrate combined with the washing liquid with crystals of the compound of formula 16-(R)-10, cooling the suspension to 0-5° C. and stirring while maintaining the temperature, followed by filtering, washing and drying the precipitated crystals, thereby obtaining crystals $K_{r2}$; and optionally (c) suspending the previously filtered crystals $K_{r1}$ in the filtrate combined with the washing liquid, refluxing the suspension, followed by cooling the mixture to 25-35° C. and stirring while maintaining the temperature, followed by filtering, washing and drying the precipitated crystals, thereby obtaining crystals $K_{r3}$; and (d) seeding the filtrate combined with the washing liquid with crystals of the compound of formula 16-(R)-10, cooling to 0-5° C. and stirring while maintaining the temperature, followed by filtering, washing and drying the precipitated crystals, thereby obtaining crystals $K_{r4}$, wherein compound of formula 16-(S)-10 is obtained as crystals $K_{r1}$ and $K_{r3}$ in step (a) and in optional step (c), and compound of formula 16-(R)-10 is obtained as crystals $K_{r2}$ and $K_{r4}$ in step (b) and in optional step (d).

4. A process according to claim 3, comprising a further step of recrystallizing the crystals $K_{r2}$ and/or $K_{r4}$ from a solvent selected from $C_{1-3}$ alcohols, tert-butyl methyl ether and their mixtures; or from a mixture of said solvents with dichloromethane.

5. A process according to claim 3, comprising a further step of epimerizing the obtained crystals $K_{r1}$ or $K_{r3}$ under acidic or basic conditions, followed by repeating the fractional crystallization of claim 3.

6. A process according to claim 5, wherein the epimerization is carried out in toluene with para-toluenesulfonic acid at about 65-75° C. by stirring during about 15-20 hours, or in ethyl acetate in the presence of silica gel, with triethyl amine at about 55-65° C. by stirring during about 10-14 hours.

7. A process according to claim 1, wherein the 15-oxo group of the compound of formula 16-(R)-10 is reduced with an aqueous solution of sodium borohydride in the presence of silica gel.

8. A process according to claim 2, wherein the 15-oxo group of the compound of formula 16-(R)-10 is reduced with an aqueous solution of sodium borohydride in the presence of silica gel.

9. A process according to claim 3, wherein the 15-oxo group of the compound of formula 16-(R)-10 is reduced with an aqueous solution of sodium borohydride in the presence of silica gel.

10. A process according to claim 1, wherein the compound of formula 1 is isolated by chromatography.

11. A process according to claim 1, wherein the obtained compound of formula 1 is crystallized from an ether type solvent or solvent mixture.

12. A process according to claim 1, wherein the compound of formula 16-(R,S)-10 is prepared by reacting an aldehyde of formula 9 with a racemic phosphonate of formula 3-(R,S)-4:

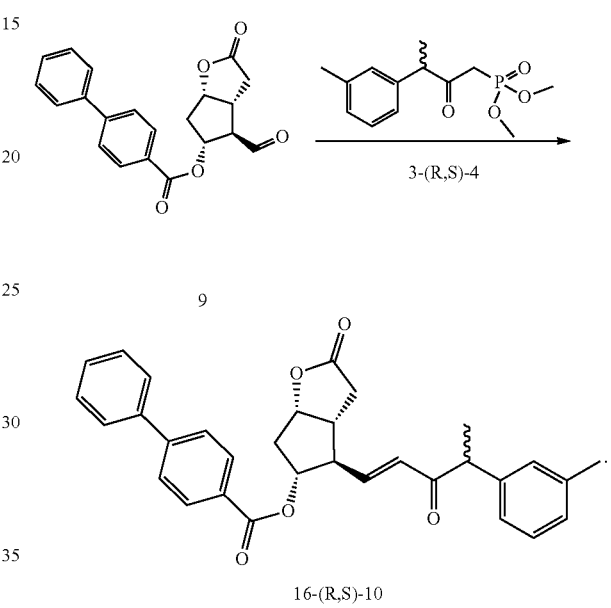

13. A process according to claim 12, wherein the reaction is carried out with potassium hydroxide base at about 20 to 25° C., or with sodium hydride at about 0 to 10° C.

14. A process according to claim 12, wherein the racemic phosphonate of formula (3-(R,S)-4) is prepared by the following reaction scheme, according to variant A) or B):

A).

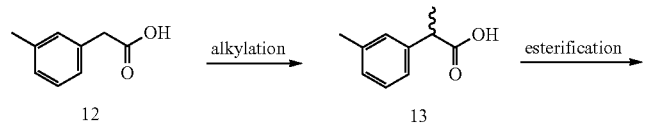

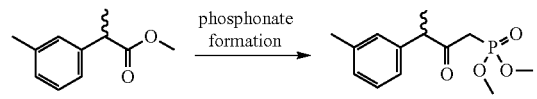

B.)

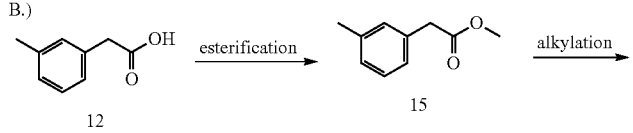

wherein, variant A) comprises:

alkylating methylphenylacetic acid of formula 12;

converting the resulting methylphenylpropionic acid of formula 13 into a methyl ester of formula 14 using methanol in the presence of an acid;

followed by reacting the methyl ester of formula 14 with dimethyl methylphosphonate (DMMP) in the presence of a strong base, thereby obtaining racemic phosphonate of formula 3-(R,S)-4;

and variant B) comprises:

converting methylphenylacetic acid of formula 12 into methylphenylacetic acid methyl ester of formula 15 using methanol in the presence of an acid;

alkylating the methylphenylacetic acid methyl ester of formula 15, thereby obtaining methyl ester of formula 14;

followed by reacting the methyl ester of formula 14 with dimethyl methylphosphonate (DMMP) in the presence of a strong base, thereby obtaining racemic phosphonate of formula 3-(R,S)-4.

15. A compound selected from:

a compound of formula 16-(R,S)-10:

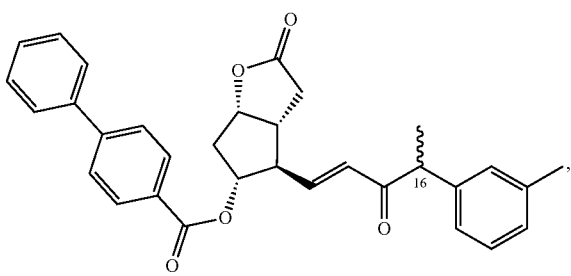

16-(R,S)-10 a compound of formula 16-(R)-10:

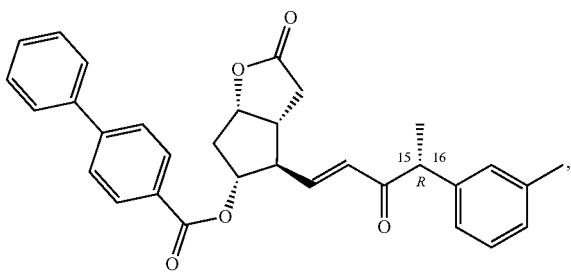

16-(R)-10 a compound of formula 16-(S)-10:

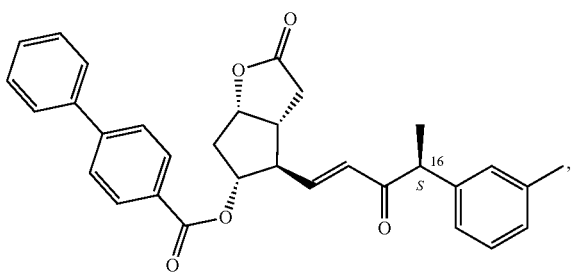

16-(S)-10 and a compound of formula 15-(R,S), 16-(R)-11:

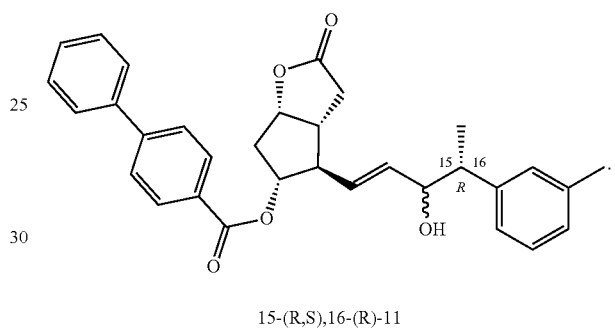

15-(R,S),16-(R)-11

16. A process for the fractional crystallization of the compound of formula 16-(R,S)-10,

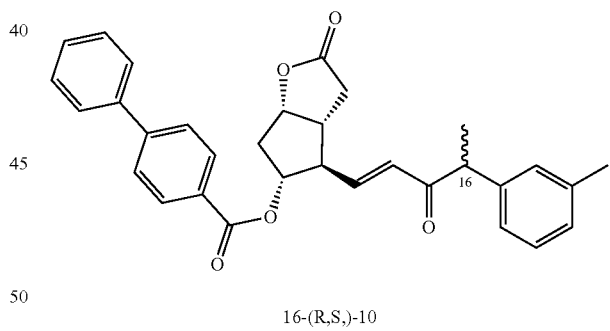

16-(R,S,)-10 using a solvent selected from $C_{1-3}$ alcohols, tert-butyl methyl ether and their mixtures; comprising (a) suspending the compound of formula 16-(R,S)-10 in the solvent, refluxing the suspension, followed by cooling the mixture to 25-35° C. and stirring while maintaining the temperature, followed by filtering, washing and drying the precipitated crystals, thereby obtaining crystals $K_{r1}$;

(b) seeding the filtrate combined with the washing liquid with crystals of the compound of formula 16-(R)-10, cooling the suspension to 0-5° C. and stirring while maintaining the temperature, followed by filtering, washing and drying the precipitated crystals, thereby obtaining crystals $K_{r2}$; and optionally (c) suspending the previously filtered crystals $K_{r1}$ in the filtrate combined with the washing liquid, refluxing the suspension, followed by cooling the mixture to 25-35° C. and stirring while maintaining the temperature, followed by filtering, washing and drying the precipitated crystals, thereby obtaining crystals $K_{r3}$; and (d) seeding the filtrate combined with the washing liquid with crystals of the compound of formula 16-(R)-10, cooling to 0-5° C. and stirring while maintaining the temperature, followed by filtering, washing and drying the precipitated crystals, thereby obtaining crystals $K_{r4}$, wherein compound of formula 16-(S)-10 is obtained as crystals $K_{r1}$ and $K_{r3}$ in step (a) and in optional step (c), and compound of formula 16-(R)-10 is obtained as crystals $K_{r2}$ and $K_{r4}$ in step (b) and in optional step (d), and optionally, recrystallizing the obtained crystals from a solvent selected from $C_{1-3}$ alcohols, tert-butyl methyl ether and their mixtures; or from a mixture of said solvents with dichloromethane.

17. A process for the preparation of the compound of formula 16-(S)-10,

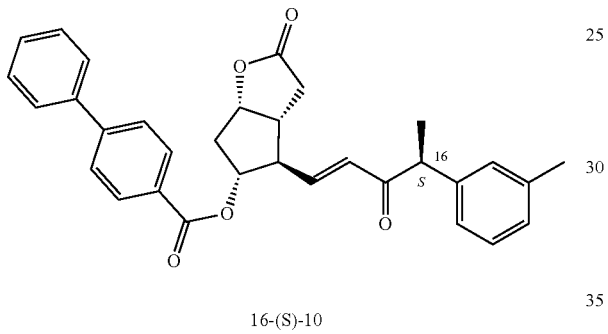

16-(S)-10 comprising (a) suspending a compound of formula 16-(R,S)-10 in a solvent selected from $C_{1-3}$ alcohols, tert-butyl methyl ether and their mixtures, refluxing the suspension, followed by cooling the mixture to 25-35° C. and stirring while maintaining the temperature, followed by filtering, washing and drying the precipitated crystals, thereby obtaining crystals $K_{r1}$;

and optionally (b) seeding the filtrate combined with the washing liquid with crystals of the compound of formula 16-(R)-10, cooling the suspension to 0-5° C. and stirring while maintaining the temperature, followed by filtering the precipitated crystals; and (c) suspending the previously filtered crystals $K_{r1}$ in the filtrate, refluxing the suspension, followed by cooling the mixture to 25-35° C. and stirring while maintaining the temperature, followed by filtering, washing and drying the precipitated crystals, thereby obtaining crystals $K_{r3}$;

and optionally, recrystallizing the obtained crystals $K_{r1}$ or $K_{r3}$ from a mixture of dichloromethane and a solvent selected from $C_{1-3}$ alcohols, tert-butyl methyl ether and their mixtures; thereby obtaining the compound of formula 16-(S)-10.

18. A process according to claim 16, wherein the solvent is selected from methanol, tert-butyl methyl ether and their mixtures.

* * * * *